US010188639B2

(12) United States Patent
DeWitt et al.

(10) Patent No.: US 10,188,639 B2
(45) Date of Patent: Jan. 29, 2019

(54) METHODS OF TREATING NEUROLOGICAL, METABOLIC, AND OTHER DISORDERS USING ENANTIOPURE DEUTERIUM-ENRICHED PIOGLITAZONE

(71) Applicant: DeuteRx, LLC, Andover, MA (US)

(72) Inventors: Sheila DeWitt, Auburn, NH (US); Vincent Jacques, Somerville, MA (US); Leonardus H. T. van der Ploeg, Newton, MA (US)

(73) Assignee: DeuteRx, LLC, Andover, MA (US)

( * ) Notice: Subject to any disclaimer, the term of this patent is extended or adjusted under 35 U.S.C. 154(b) by 0 days.

(21) Appl. No.: 15/109,533

(22) PCT Filed: Jan. 15, 2015

(86) PCT No.: PCT/US2015/011493
§ 371 (c)(1),
(2) Date: Oct. 7, 2016

(87) PCT Pub. No.: WO2015/109037
PCT Pub. Date: Jul. 23, 2015

(65) Prior Publication Data
US 2016/0331737 A1 Nov. 17, 2016

Related U.S. Application Data

(60) Provisional application No. 61/931,808, filed on Jan. 27, 2014, provisional application No. 61/927,708, filed on Jan. 15, 2014.

(51) Int. Cl.
A61K 31/425 (2006.01)
A61K 31/426 (2006.01)
A61K 31/427 (2006.01)
A61K 31/4439 (2006.01)
C07D 417/12 (2006.01)
A61K 9/00 (2006.01)

(52) U.S. Cl.
CPC ........ A61K 31/4439 (2013.01); A61K 9/0053 (2013.01); C07D 417/12 (2013.01); A61K 31/425 (2013.01); A61K 31/426 (2013.01); A61K 31/427 (2013.01)

(58) Field of Classification Search
CPC ... A61K 31/425; A61K 31/426; A61K 31/427
USPC ........................................ 514/369, 365, 367
See application file for complete search history.

(56) References Cited

U.S. PATENT DOCUMENTS

| | | | |
|---|---|---|---|
| 4,421,865 A | 12/1983 | Shen | |
| 4,687,777 A | 8/1987 | Meguro et al. | |
| 5,149,820 A | 9/1992 | Borretzen et al. | |
| 5,441,971 A | 8/1995 | Sohda et al. | |
| 6,191,154 B1 * | 2/2001 | Landreth | A61K 31/00 514/365 |
| 6,221,335 B1 | 4/2001 | Foster | |
| 6,334,997 B1 | 1/2002 | Foster et al. | |
| 6,432,993 B1 | 8/2002 | Fujita et al. | |
| 6,440,710 B1 | 8/2002 | Keinan et al. | |
| 6,603,008 B1 | 8/2003 | Ando et al. | |
| 6,706,746 B2 | 3/2004 | Fujita et al. | |
| 7,517,990 B2 | 4/2009 | Ito et al. | |
| 8,067,450 B2 | 11/2011 | Colca et al. | |
| 8,236,786 B2 | 8/2012 | Finch et al. | |
| 8,263,631 B2 | 9/2012 | Fujiwara et al. | |
| 8,389,556 B2 | 3/2013 | Colca et al. | |
| 8,722,710 B2 * | 5/2014 | Czarnik | C07D 417/12 514/342 |
| 8,969,581 B2 | 3/2015 | DeWitt | |
| 9,123,444 B2 | 9/2015 | Subramaniam et al. | |
| 9,416,117 B2 | 8/2016 | DeWitt | |
| 9,782,395 B2 | 10/2017 | Garcia Collazo et al. | |
| 9,833,445 B2 | 12/2017 | DeWitt | |
| 9,925,175 B2 | 3/2018 | Czarnik | |
| 2003/0181494 A1 | 9/2003 | Neogi et al. | |
| 2004/0253180 A1 | 12/2004 | Foster et al. | |
| 2007/0082929 A1 | 4/2007 | Gant et al. | |
| 2007/0197695 A1 | 8/2007 | Potyen et al. | |
| 2009/0028868 A1 | 1/2009 | Fujiwara et al. | |
| 2009/0076093 A1 | 3/2009 | Czarnik | |
| 2009/0082405 A1 | 3/2009 | Czarnik | |
| 2012/0015982 A1 | 1/2012 | Colca et al. | |
| 2014/0221369 A1 | 8/2014 | DeWitt | |

(Continued)

FOREIGN PATENT DOCUMENTS

EP 1628646 B1 7/2010
WO WO-92/018501 A1 10/1992

(Continued)

OTHER PUBLICATIONS

U.S. Appl. No. 15/088,472, filed Apr. 1, 2016, Deuterium-Enriched Pioglitazone.
U.S. Appl. No. 15/226,240, filed aug. 2, 2016, 5-Deutero-2,4-Thiazolidinedione Derivatives and Compositions Comprising and Methods of Using the Same.
Aithal et al., "Randomized, Placebo-Controlled Trial of Pioglitazone in Nondiabetic Subjects with Nonalcoholic Steatohepatitis," *Gastroenterology* (2008), vol. 135, pp. 1176-1184.
Baillie, T., "The Use of Stable Isotopes in Pharmacological Research", Pharmacological Reviews, 33(2):81-132 (1981).
Bharatam et al., "Rapid Racemization in Thiazolidinediones: A Quantum Chemical Study", J. Phys. Chem. A., 108:3784-3788 (2004).

(Continued)

Primary Examiner — Kevin E Weddington
(74) Attorney, Agent, or Firm — Goodwin Procter LLP

(57) ABSTRACT

The invention provides enantiopure deuterium-enriched pioglitazone, pharmaceutical compositions, and methods of treating neurological disorders, cancer, respiratory disorders, metabolic disorders, and other disorders using enantiopure deuterium-enriched pioglitazone. A preferred aspect of the invention provides methods of treating Alzheimer's disease, non-small cell lung cancer, hepatocellular carcinoma, and chronic obstructive pulmonary disease using enantiopure deuterium-enriched pioglitazone.

20 Claims, 14 Drawing Sheets

(56) References Cited

U.S. PATENT DOCUMENTS

| | | |
|---|---|---|
| 2014/0243377 A1 | 8/2014 | Czarnik |
| 2014/0275180 A1 | 9/2014 | DeWitt |
| 2015/0284346 A1 | 10/2015 | DeWitt |
| 2016/0354355 A1 | 12/2016 | Czarnik |
| 2017/0049762 A1 | 2/2017 | DeWitt |
| 2018/0117026 A1 | 5/2018 | DeWitt et al. |
| 2018/0118730 A1 | 5/2018 | DeWitt et al. |
| 2018/0125827 A1 | 5/2018 | DeWitt et al. |
| 2018/0125834 A1 | 5/2018 | DeWitt et al. |
| 2018/0133204 A1 | 5/2018 | DeWitt |

FOREIGN PATENT DOCUMENTS

| | | |
|---|---|---|
| WO | WO-1995/26325 A2 | 10/1995 |
| WO | WO-1999/018081 A1 | 4/1999 |
| WO | WO-2003/033494 A1 | 4/2003 |
| WO | WO-2003/059271 A2 | 7/2003 |
| WO | WO-2004/073622 A2 | 9/2004 |
| WO | WO-2005/058827 A1 | 6/2005 |
| WO | WO-2006/064826 A1 | 6/2006 |
| WO | WO-2006/083781 A1 | 8/2006 |
| WO | WO-2006/126673 A1 | 11/2006 |
| WO | WO-2007/007656 A1 | 1/2007 |
| WO | WO-2007/100027 A1 | 9/2007 |
| WO | WO-2007/109024 A2 | 9/2007 |
| WO | WO-2007/136129 A1 | 11/2007 |
| WO | WO-2008/099944 A1 | 8/2008 |
| WO | WO-2009/038681 A1 | 3/2009 |
| WO | WO-2010/015818 A1 | 2/2010 |
| WO | WO-2010/150014 A1 | 12/2010 |
| WO | WO-2011/017244 A1 | 2/2011 |
| WO | WO-2011/065420 A1 | 6/2011 |
| WO | WO-2011/098799 A2 | 8/2011 |
| WO | WO-2011/098801 A1 | 8/2011 |
| WO | WO-2011/100685 A2 | 8/2011 |
| WO | WO-2011/133441 A2 | 10/2011 |
| WO | WO-2013/011402 A1 | 1/2013 |
| WO | WO-2013/056232 A2 | 4/2013 |
| WO | WO-2013/134626 A1 | 9/2013 |
| WO | WO-2014/121036 A1 | 8/2014 |
| WO | WO-2014/152843 A1 | 9/2014 |
| WO | WO-2015/109037 A1 | 7/2015 |

OTHER PUBLICATIONS

Boettcher et al., "Meta-analysis: Pioglitazone Improves Liver Histology and Fibrosis in Patients with Non-Alcoholic Steatohepatitis," Aliment Pharmacol Ther, vol. 35, pp. 66-75 (2012).

Browne, T., "Stable Isotope Techniques in Early Drug Development: An Economic Evaluation", J Clin Pharmacol, 38:213-220 (1998).

Buteau, K., "Deuterated Drugs: Unexpectedly Nonobvious?", 10 J. High Tech. L. 22 (2009) (53 pages).

Cabrero et al., "Peroxisome Proliferator-Activated Receptors and the Control of Inflammation", Current Drug Target—Inflammation & Allergy, 1(3):243-248 (2002) (Abstract).

Chalasani et al., "The Diagnosis and Management of Non-Alcoholic Fatty Liver Disease: Practice Guideline by the American Association for the Study of Liver Diseases, American College of Gastroenterology, and the American Gastroenterological Association," Hepatology (2012), vol. 55, No. 6, pp. 2005-2023.

Chen et al., "Insulin Resistance and Metabolic Derangements in Obese Mice Are Ameliorated by a Novel Peroxisome Proliferator-activated Receptor γ-sparing Thiazolidinedione", J. Biol. Chem., 287(28):23537-23548 (2012).

Cherrah et al., "Study of Deuterium Isotope Effects on Protein Binding by Gas Chromatography/Mass Spectrometry. Caffeine and Deuterated Isotopomers", Biomedical and Environmental Mass Spectrometry, 14:653-657 (1987).

Colca et al., "Identification of a Mitochondrial Target of Thiazolidinedione Insulin Sensitizers (mTOT)-Relationship to Newly Identified Mitochondrial Pyruvate Carrier Proteins", PLOS One, 8(5)e61551:1-10 (2013).

Dyck et al., "Effects of Deuterium Substitution on the Catabolism of β-Phenylethylamine: An in Vivo Study", J Neurochem, 46(2):399-404 (1986).

Federal Register "Examination guidelines" p. 1-34, Sep. 1, 2010.

Federico, et al., "Focus on emerging drugs for the treatment of patients with non-alcoholic fatty liver disease," World Journal of Gastroenterology (2014), vol. 20, pp. 16841-16857.

Foster, A., "Deuterium Isotope Effects in the Metabolism of Drugs and Xenobiotics: Implications for Drug Design", Adv. Drug Res., 14:2-40 (1985).

Gouyette, A., "Synthesis of Deuterium-labelled Elliptinium and its Use in Metabolic Studies", Biomedical and Environmental Mass Spectrometry, 15:243-247 (1988).

Harbeson et al., "Deuterium in Drug Discovery and Development", Annual Reports in Med Chem, 46:403-417 (2011).

Honma et al., "The Metabolism of Roxatidine Acetate Hydrochloride", Drug Metabolism and Disposition, 15(4):551-559 (1987).

Hutt et al., "The Chiral Switch: The Development of Single Enantiomer Drugs from Racemates", ACTA Facult. Pharm. Univ. Comenianae, 50:7-23 (2003).

International Search Report and Written Opinion for International Application No. PCT/US2015/011493 dated Mar. 6, 2015 (10 pages).

International Search Report and Written Opinion for PCT/US2014/014083 dated May 16, 2014 (12 pages).

International Search Report and Written Opinion for PCT/US2014/027943 dated Jul. 10, 2014 (15 pages).

Jamali et al., "Investigation of racemisation of the enantiomers of glitazone drug compounds at different pH using chiral HPLC and chiral CE", J. Pharm. and Biomed. Anal., 46:82-87 (2008).

Kaufman et al., "Deuterium Enrichment of Vitamin A at the C20 Position Slows the Formation of Detrimental Vitamin A Dimers in Wild-type Rodents", J. Biol. Chem., 286(10):7958-7965 (2011).

Kawaguchi et al., "Pioglitazone prevents hepatic steatosis, fibrosis, and enzyme-altered lesions in rat liver cirrhosis induced by a choline-deficient L-amino acid-defined diet," Biochemical and Biophysical Research Communications, (2004), vol. 315, pp. 187-195.

Kawai et al., "Hydrogen-Rich Water Prevents Progression of Non-alcoholic Steatohepatitis and Accompanying Hepatocarcinogenesis in Mice," Hepatology (2012), vol. 56, pp. 912-921.

Leclercq et al., "Intrahepatic insulin resistance in a murine model of steatohepatitis: effect of PPARγ agonist pioglitazone," Laboratory Investigation (2007), vol. 87, pp. 56-65.

Lin et al., "Dose effect of thiazolidinedione on cancer risk in type 2 diabetes mellitus patients: a six-year population-based cohort study," Journal of Clinical Pharmacy and Therapeutics (2014), vol. 39, pp. 354-360.

Lomonaco et al., "Nonalcoholic Fatty Liver Disease: Current Issues and Novel Treatment Approaches," Drugs, vol. 73, pp. 1-14 (2013).

Lutchman et al., "The Effects of Discontinuing Pioglitazone in Patients with Nonalcoholic Steatohepatitis," Hepatology (2007) vol. 46, pp. 424-429.

Maltais et al., "In Vitro and In Vivo Isotope Effects with Hepatitis C Protease Inhibitors: Enhanced Plasma Exposure of Deuterated Telaprevir versus Telaprevir in Rats", J. Med. Chem. (2009) vol. 52, pp. 7993-8001.

Mislow et al., "A Note on Steric Isotope Effects. Conformational Kinetic Isotope Effects in the Racemization of 9,10-Dihydro-4,5-Dimethylphenanthrene", J. Am. Chem. Soc. 85:1199-1200 (1963).

Motani et al., "INT131: A Selective Modulator of PPARγ", J. Mol. Biol., 386:1301-1311 (2009).

Nassar et al., "Improving the decision-making process in the structural modification of drug candidates: enhancing metabolic stability", Drug Discovery Today, 9(23):1020-1028 (2004).

Nelson et al., "The Use of Deuterium Isotope Effects to Probe the Active Site Properties, Mechanism of Cytochrome P450-Catalyzed Reactions, and Mechanisms of Metabolically Dependent Toxicity", Drug Metabolism and Disposition, 31(12):1481-1498 (2003).

Parks et al., "Differential Activity of Rosiglitazone Enantiomers at PPARγ", Bioorg. & Medicinal Chem. Letters, 8:3657-3658 (1998).

Pfutzner et al., "Pioglitazone: update on an oral antidiabetic drug with antiatherosclerotic effects", Expert Opin. Pharmacother., 8(12):1985-1998 (2007).

(56) References Cited

OTHER PUBLICATIONS

Pieniaszek, Jr., et al., "Moricizine Bioavailability via Simultaneous, Dual, Stable Isotope Administration: Bioequivalence Implications", J Clin Pharmacol, 39:817-825 (1999).
Promrat et al., "A Pilot Study of Pioglitazone Treatment for Nonalcoholic Steatohepatitis," Hepatology (2004), vol. 39, pp. 188-196.
Sanyal et al., "A Pilot Study of Vitamin E Versus Vitamin E and Pioglitazone for the Treatment of Nonalcoholic Steatohepatitis," *Clinical Gastroenterology and Hepatology* (2004), vol. 2, pp. 1107-1115.
Sanyal et al., "Pioglitazone, Vitamin E, or Placebo for Nonalcoholic Steatohepatitis," *The New England Journal of Medicine*, (2010) vol. 362, pp. 1675-1685.
Shao et al., "Derivatives of tramadol for increased duration of effect", Bioorg. Med. Chem. Lett. 16:691-694 (2006).
Smith et al., "Non-Alcoholic Fatty Liver Disease," Critical Reviews in Clinical Laboratory Sciences, vol. 48, pp. 97-113 (2011).
Sohda et al., "Studies on Antidiabetic Agents. XII.1) Synthesis and Activity of the metabolites of (±)-5-[p-[2-(5-Ethyl-2-pyridypethoxy]benzyl]-2,4-thiazolidinedione (Pioglitazone)", Chem. Pharm. Bull., 43(12):2168-2172 (1995).
Uto et al., "The peroxisome proliferator-activated receptor-γ agonist, pioglitazone, inhibits fat accumulation and fibrosis in the livers of rats fed a choline-deficient, L-amino acid-defined diet," *Hepatology Research* (2005), vol. 32, pp. 235-242.
Van Wagner et al., "The role of insulin-sensitizing agents in the treatment of nonalcoholic steatohepatitis," *Ther Adv Gastroenterol* (2011) vol. 4, pp. 249-263.
Wiberg, K., "The Deuterium Isotope Effect", Chem. Rev., 55(4):713-743 (1955).
Yarnell, A., "Heavy-Hydrogen Drugs Turn Heads, Again", Chemical & Engineering News, 87(25):36-39 (2009).
Zhang et al., "Thiazolidinediones Improve Hepatic Fibrosis in Rats with Non-Alcoholic Steatohepatitis by Activating the Adenosine Monophosphate-Activated Protein Kinase Signalling Pathway," Clinical and Experimental Pharmacology and Physiology, vol. 39, pp. 1026-1033 (2012).
Zhu Y. et al., "Deuterated Clopidogrel Analogues as a New Generation of Antiplatelet Agents", *ACS Med. Chem. Lett.* 2013, vol. 4, Issue 3, pp. 349-352.
Dorwald, "Side Reactions in Organic Synthesis," Wiley, pp. IX of preface pp. 1-15 (2005).
Colca et al., "Identification of a Novel Mitochondrial Protein ("mitoNEET") Cross-linked Specifically by a Thiazolidinedione Photoprobe", Am J Physiol Endrocrinol Metab, (2004), 286(2):E252-60.
Divakaruni et al., "Thiazolidinediones are Acute, Specific Inhibitors of the Mitochondrial Pyruvate Carrier," Proc Natl Acad Sci USA, (2013), 110(14):5422-7.
Foster, "Deuterium Isotope Effects in Studies of Drug Metabolism," Trends Pharmacol Sci, (1984), 5:524-7.
Jaakkola et al., "Montelukast and Zafirlukast do not Affect the Pharmacokinetics of the CYP2C8 Substrate Pioglitazone," Eur J Clin Pharmacol, (2006), 62(7):503-9.
Jaakkola et al., "Pioglitazone is Metabolized by CYP2C8 and CYP3A4 in vitro. Potential for Interactions with CYP2C8 Inhibitors," Basic Clin Phamacol Toxicol, (2006), 99(1):44-51.
Stedman and Barclay, "Review Article: Comparison of the Pharmacokinetics, Acid Suppression and Efficacy of Proton Pump Inhibitors," Aliment Pharmacol Ther, (2000), 14(8):963-78.
Tilg and Moschen, "Evolving Therapies for Non-Alcoholic Steatohepatitis," Expert Opin Drug Discov, (2014), 9(6):687-96.
Haskins, N. J. "The Application of Stable Isotopes in Biomedical Research," *Biomedical Mass Spectrometry*, 9 (7), 1982, 269-277.
Kushner, D.J. et al. "Pharmacological Uses and Perspectives of Heavy Water and Deuterated Compounds," *Canadian Journal of Physiology and Pharmacology*, 1999, 77(2), 79-88.
Tonn et al. "Simultaneous Analysis of Diphenhydramine and a Stable Isotope Analog ($^2H_{10}$)Diphenydramine Using Capillary Gas Chromatography with Mass Selective Detection in Biological Fluids from Chronically Instrumented Pregnant Ewes," *Biological Mass Spectrometry*, 22 (11) 1993, 633-642.
Wolen, R. L."The application of stable isotopes to studies of drug bioavailability and bioequivalence," *J. Clin. Pharm.* (1986) vol. 26, pp. 419-424.
Shao, L. & Hewitt, M.C. "The Kinetic Isotope Effect in the Search for Deuterated Drugs," *Drug News & Perspectives*, 2010, vol. 23, No. 6, pp. 398-404.
Yamamoto et al., "Synthesis and Configurational Stability of (S)- and (R)-Deuteriothalidomides", Chem. Pharm. Bull. 58(1):110-112 (2010).
Fisher et al., "The complexities inherent in attempts to decrease drug clearance by blocking sites of CYP-mediated metabolism", *Curr. Opin. Drug Disc. Dev.*, 9(1):101-109 (2006).
Wade, D., "Deuterium isotope effects on noncovalent interactions between molecules", *Chemico-Biological Interactions*, 117 p. 191-217 (1999).
Woo, H.Y, et al., "Rescue therapy with adefovir in decompensated liver cirrhosis patients with lamivudine-resistant hepatitis B virus", Clinical and Molecular Hepatology, 2014, vol. 20, pp. 168-176.
Peng, S., et al., "An Updated Meta-Analysis of Randomized Controlled Trials Assessing the Effect of Sorafenib in Advanced Hepatocellular Carcinoma", PLOS ONE, 2014, vol. 9, No. 12, pp. e112530.
Farlow, M. R., et al., "Comparing Clinical Profiles in Alzheimer's Disease and Parkinson's Disease Dementia", Dementia and Geriatric Cognitive Disorders Extra, 2013, vol. 3, pp. 281-290.
Griebeler, M.L., et al, "Pharmacologic interventions for painful diabetic neuropathy: An umbrella systematic review and comparative effectiveness network meta-analysis", Annals of Internal Medicine, 2014, vol. 161, No. 9, pp. 639-649.
Zhou, C. et al., "Discovery of 5-aryloxy-2,4-thiazolidinediones as potent GPR40 agonists", Bioorg. Med. Chem. Lett. 2010, vol. 20, No. 3, pp. 1298-1301.
Christiansen, E. et al., "Identification of a Potent and Selective Free Fatty Acid Receptor 1 (FFA1/GPR40) Agonist with Favorable Physicochemical and in Vitro ADME Properties", J. Med. Chem. (2011) vol. 54, No. 19, pp. 6691-6703.
International Search Report and Written Opinion for PCT/US2015/011493 dated Mar. 6, 2015 (9 pages).
Hardy, T. et al. "Nonalcoholic fatty liver disease: new treatments," *Curr. Opin. Gastroenterology* (2015) vol. 31, No. 3, pp. 175-183.
Chalasani et al., "The Diagnosis and Management of Non-Alcoholic Fatty Liver Disease: Practice Guideline by the American Gastroenterological Association, American Association for the Study of Liver Diseases, and American College of Gastroenterology," *Gastroenterology* (2012), vol. 142, No. 7, pp. 1592-1609.
U.S. Appl. No. 15/917,983, filed Mar. 12, 2018, Deuterium-Enriched Pioglitazone.
U.S. Appl. No. 15/805,330, filed Nov. 7, 2017, 5-Deutero-2,4-Thiazolidinedione Derivatives and Compositions Comprising and Methods of Using the Same.
U.S. Appl. No. 15/705,541, filed Sep. 15, 2017, Combination Therapy Using Enantiopure, Oxy-Substituted, Deuterium-Enriched 5-(Benzyl)-5-Deutero-Thiazolidine-2,4-Diones for Treatment of Medical Disorders.
U.S. Appl. No. 15/705,544, filed Sep. 15, 2017, 5-Deutero-Thiazolidine-2,4-Dione Compounds and Methods of Treating Medical Disorders Using Same.
U.S. Appl. No. 15/705,545, filed Sep. 15, 2017, 5-Deutero-Thiazolidinyldione Compounds and Methods of Treating Medical Disorders Using Same.
U.S. Appl. No. 15/705,547, filed Sep. 15, 2017, Methods of Treating Bacterial Infections and Fungal Infections Using Enantiopure Deuterium-Enriched Pioglitazone.
Cusi, K. et al. "Long-Term Pioglitazone Treatment for Patients With Nonalcoholic Steatohepatitis and Prediabetes or Type 2 Diabetes Mellitus: A Randomized, Controlled Trial," *Ann. Intern. Med.* published online at doi: 10.7326/M15-1774. Published in final form as *Ann. Intern. Med.* (2016) vol. 165, No. 5, p. 305-315.
Tanis, S. P. et al. "Synthesis and Biological Activity of Metabolites of the Antidiabetic, Antihyperglycemic Agent Pioglitazone," *J. Med. Chem.* (1996) vol. 39, pp. 5053-5063.

(56) References Cited

OTHER PUBLICATIONS

Leoni, A. et al., "Novel thiazole derivatives: a patent review (2008-2012. Part 2)," *Expert Opin. Ther. Patents* (2014), vol. 24, No. 7, pp. 759-777.

Jorden, D., "World Alzheimer Day: French Doctor Denounces Routine Alzheimer Medications," dated Dec. 20, 2015. Downloaded from the Internet at URL: https://zcomm.org/znetarticle/world-alzheimer-day-french-doctor-denounces-routine-alzheimer-medications/ (4 pages).

Landreth, G. et al., "PPARγ Agonists as Therapeutics for the Treament of Alzheimer's Disease," *Neurotherapeutics: J. Am. Soc. Exper. NeuroTherapeutics* (2008), vol. 5, No. 3, pp. 481-489.

Polyzos, S. A. and Mantzoros, C. S. "Adiponectin as a target for the treament of nonalcoholic steatohepatitis with thiazolidinediones: A systematic review," *Metabolism, Clinical and Experimental* (2016), vol. 65, No. 9, pp. 1297-1306.

World Health Organization "The ICD-10 Classification of Mental and Behavioural Disorders: Diagnostic criteria for research," Geneva (1993).

Venkatesh, S. and Lipper, R. A., "Role of the Development Scientist in Compound Lead Selection and Optimization," *J. Pharm. Sci.* (2000), vol. 89, No. 2, pp. 145-154.

Mandard, S. and Patsouris, D., "Nuclear Control of the Inflammatory Response in Mammals by Peroxisome Proliferator-Activated Receptors," *PPAR Research* (2013) Article ID 613864, DOI: 10.1155/2013/613864. (23 pages).

Binda, C. et al., "Molecular Insights into Human Monoamine Oxidase B Inhibition by the Glitazone Antidiabetes Drugs," *ACS Med. Chem. Lett.* (2012), vol. 3, pp. 39-42.

\* cited by examiner

METHODS OF TREATING NEUROLOGICAL, METABOLIC, AND OTHER DISORDERS USING ENANTIOPURE DEUTERIUM-ENRICHED PIOGLITAZONE

CROSS-REFERENCE TO RELATED APPLICATIONS

This application is the national stage of International (PCT) Patent Application Serial No. PCT/US2015/011493, filed Jan. 15, 2015 which claims the benefit of and priority to United States Provisional Patent Application Ser. No. 61/927,708, filed Jan. 15, 2014, and to United States Provisional Patent Application Ser. No. 61/931,808, filed Jan. 27, 2014; the contents of each of which are hereby incorporated by reference in their entirety.

FIELD OF THE INVENTION

The invention provides enantiopure deuterium-enriched pioglitazone, pharmaceutical compositions, and methods of treating neurological disorders, cancer, respiratory disorders, metabolic disorders, and other disorders using enantiopure deuterium-enriched pioglitazone.

BACKGROUND

Peroxisome proliferator-activated receptors (PPARs) are a group of nuclear receptor proteins that function as transcription factors regulating the expression of genes. There are three subtypes of these receptors, PPAR alpha, beta, and gamma PPARs mainly regulate the expression of genes involved in the regulation of lipid and carbohydrate metabolism. These receptors are also involved in the regulation of inflammatory processes, reproduction, carcinogenesis, and other physiological processes in the body. Treatment of a variety of medical disorders (e.g., Alzheimer's disease, cancer, and chronic obstructive pulmonary disease) has been linked to modulating the activity (e.g., activation) of certain PPARs.

Therapeutics that modulate PPARs have been commercialized for treating medical disorders, such as metabolic disorders. One such example is pioglitazone hydrochloride, which has been approved by the United States Food and Drug Administration as an adjunct to diet and exercise to improve glycemic control in adults with type 2 diabetes mellitus in multiple clinical settings. Pioglitazone hydrochloride is marketed under the registered trademark ACTOS® and the prescribing information for ACTOS® explains that pioglitazone is an agonist of PPAR gamma. The commercialized form of pioglitazone hydrochloride is a racemic mixture and adverse side effects have been reported in patients receiving this therapeutic, including, for example, edema and increased incidence of bone fracture.

Pioglitazone and other thiazolidinediones have been shown to have anti-inflammatory activity, part of which seems to be mediated by a mechanism not involving PPARs (Curr Drug Targets Inflamm Allergy 2002, 1(3):243-248). Recently, thiazolidinediones have also been shown to bind mitochondrial membrane proteins, including the mitochondrial target of thiazolidinedione (mTOT), and the thiazolidinediones may modulate mitochondrial metabolism through this direct binding. See, for example, PLoS One. 2013; 8(5): e61551; PNAS 2013, 110(14), 5422-5427; Am J Physiol Endocrinol Metab 2004, 286, E252-260.

Due to the increasing number of patients suffering from disorders such as those mentioned above, and the limitations of existing therapies, such as adverse side effects, there is a need for new therapeutic agents for treating medical disorders in which modulation of PPAR, anti-inflammatory, and/or mTOT activity are predicted to be beneficial. The present invention addresses these needs and provides other related advantages.

SUMMARY OF THE INVENTION

The invention provides enantiopure deuterium-enriched pioglitazone, pharmaceutical compositions, and methods of treating neurological disorders, cancer, respiratory disorders, metabolic disorders, and other disorders using the enantiopure deuterium-enriched pioglitazone. The deuterated pioglitazone contains deuterium enrichment at the chiral center of pioglitazone and optionally in other locations in the compound. Further, the deuterium-enriched pioglitazone is provided in enantiomerically pure form. This enantiomerically pure, deuterium-enriched pioglitazone provides for a better therapeutic agent than non-deuterated pioglitazone and/or racemic mixtures of deuterium-enriched pioglitazone.

Accordingly, one aspect of the invention provides a deuterium-enriched compound of Formula I for use in the therapeutic methods and pharmaceutical compositions described herein. Desirably, the deuterium-enriched compound of Formula I has an optical purity of at least 75% enantiomeric excess. Formula I is represented by:

(I)

or a pharmaceutically acceptable salt thereof, wherein:
$A^1$, $A^2$, $A^3$, and $A^4$ are independently $-C(R^9)(R^{10})-$;
$A^5$ is $-C(R^{11})(R^{12})(R^{13})$;
$R^1$, $R^2$, $R^3$, $R^4$, $R^5$, $R^6$, $R^7$, and $R^8$ are independently H or D;
$R^9$, $R^{10}$, $R^{11}$, $R^{12}$, and $R^{13}$ each represent independently for each occurrence H or D; and
Z is H or D, provided that the abundance of deuterium in Z is at least 30%.

In certain embodiments, the deuterium-enriched compound used in the therapeutic methods and pharmaceutical compositions has the following structure:

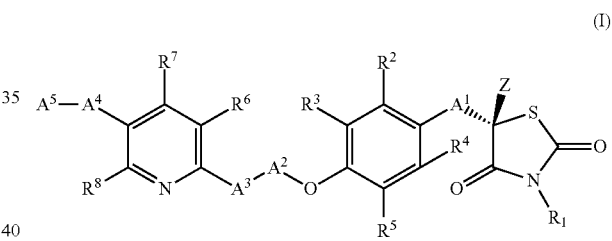

or is a pharmaceutically acceptable salt thereof, each having an optical purity of at least 90% enantiomeric excess.

Another aspect of the invention provides a deuterium-enriched compound of Formula II for use in the therapeutic methods and pharmaceutical compositions described herein.

Desirably, the deuterium-enriched compound of Formula II has an optical purity of at least 75% enantiomeric excess. Formula II is represented by:

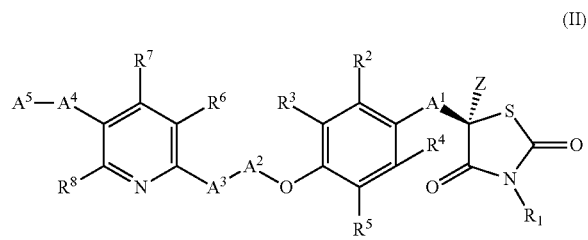

(II)

or a pharmaceutically acceptable salt thereof, wherein:
$A^1$, $A^2$, $A^3$, and $A^4$ are independently —C($R^9$)($R^{10}$)—;
$A^5$ is —C($R^{11}$)($R^{12}$)($R^{13}$);
$R^1$, $R^2$, $R^3$, $R^4$, $R^5$, $R^6$, $R^7$, and $R^8$ are independently H or D;
$R^9$, $R^{10}$, $R^{11}$, $R^{12}$, and $R^{13}$ each represent independently for each occurrence H or D; and
Z is H or D, provided that the abundance of deuterium in Z is at least 30%.

In certain embodiments, the deuterium-enriched compound used in the therapeutic methods and pharmaceutical compositions has the following structure:

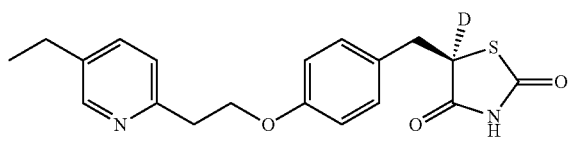 [SMILES: [2H][C@]1(Cc2ccc(OCCc3ccc(CC)cn3)cc2)SC(=O)NC1=O]

or is a pharmaceutically acceptable salt thereof, each having an optical purity of at least 90% enantiomeric excess.

The deuterium-enriched compounds are particularly useful in the treatment of medical disorders. Exemplary medical disorders include, for example, neurological disorders, cancer, respiratory disorders, and metabolic disorders. The compounds are typically administered to a patient in the form of a pharmaceutical composition. Particularly preferred medical disorders include, for example, Alzheimer's disease and other forms of cognitive impairment, non-small cell lung cancer, hepatocellular carcinoma, and chronic obstructive pulmonary disease.

Accordingly, one aspect of the invention provides a method of treating a neurological disorder selected from the group consisting of Alzheimer's disease, Parkinson's disease, amyotrophic lateral sclerosis, Friedreich's ataxia, autism spectrum disorder, depression, mild cognitive impairment, Down syndrome, neurodegeneration, adrenoleukodystrophy, Huntington's disease, stroke, traumatic brain injury, substance abuse, spinal cord injury, neuronal injury, major depression or bipolar disorder comorbid with metabolic syndrome, and a neurological disorder caused by functional mitochondrial impairment. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Another aspect of the invention provides a method of treating a disorder selected from the group consisting of cancer, a metabolic disorder, a symptom of hepatitis, a cardiovascular disease, polycystic ovary syndrome, and a skin defect caused by exposure to ultraviolet radiation. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II. In certain embodiments, the disorder is cancer. In certain embodiments, the cancer is lung cancer, hepatocellular carcinoma, astrocytoma, glioma, glioblastoma, meningioma, liver cancer, lymphoma, melanoma, multiple myeloma, pancreatic cancer, colorectal cancer, pituitary cancer, thyroid cancer, esophageal cancer, prostate cancer, ear cancer, nose cancer, throat cancer, kidney cancer, breast cancer, stomach cancer, or uterine cancer. In certain embodiments, the cancer is lung cancer, hepatocellular carcinoma, astrocytoma, glioma, glioblastoma, meningioma, liver cancer, lymphoma, melanoma, multiple myeloma, pancreatic cancer, colorectal cancer, pituitary cancer, thyroid cancer, esophageal cancer, or prostate cancer. In certain embodiments, the cancer is non-small cell lung cancer or hepatocellular carcinoma. In certain embodiments, the disorder is a metabolic disorder, non-alcoholic fatty liver disease, viral hepatitis, liver cirrhosis, liver fibrosis, diabetic retinopathy, diabetic neuropathy, diabetic nephropathy, beta cell depletion, insulin resistance in a patient with congenital adrenal hyperplasia treated with a glucocorticoid, dysmetabolism in peritoneal dialysis patients, reduced insulin secretion, improper distribution of brown fat cells and white fat cells, obesity, or improper modulation of leptin levels. In certain embodiments, the disorder is a metabolic disorder selected from the group consisting of non-alcoholic fatty liver disease, diabetic retinopathy, diabetic neuropathy, diabetic nephropathy, beta cell depletion, insulin resistance in a patient with congenital adrenal hyperplasia treated with a glucocorticoid, dysmetabolism in peritoneal dialysis patients, reduced insulin secretion, improper distribution of brown fat cells and white fat cells, obesity, and improper modulation of leptin levels. In certain embodiments, the disorder is cardiovascular disease, such as hypertension, hyperlipidemia, atherosclerosis, improper vascular function, dyslipidemia, stenosis, restenosis, myocardial infarction, stroke, intracranial hemorrhage, acute coronary syndrome, stable angina pectoris, or unstable angina pectoris. In certain other embodiments, the cardiovascular disorder is intracranial hemorrhage, acute coronary syndrome, stable angina pectoris, or unstable angina pectoris. In certain other embodiments, the metabolic disorder is beta cell loss treatable by B-cell regeneration.

Another aspect of the invention provides a method of treating a respiratory disorder. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is administered by pulmonary administration, such as when the deuterium-enriched compound has the (S)-stereochemical configuration at the stereocenter of the thiazolidine-2,4-dione ring. In certain embodiments, the deuterium-enriched compound is administered by routes other than pulmonary administration.

In certain embodiments, the deuterium-enriched compound is administered by oral administration, sublingual administration, sublabial administration, rectal administration, injection, or transdermal administration. In certain embodiments, the deuterium-enriched compound is a compound of Formula I. In certain other embodiments, the deuterium-enriched compound is a compound of Formula II. In certain embodiments, the respiratory disorder is further selected from an inflammatory condition that contributes to metabolic syndrome. In certain embodiments, the respiratory disorder is chronic obstructive pulmonary disease, asthma, bronchitis, cystic fibrosis, pulmonary edema, pulmonary embolism, pulmonary arterial hypertension, pneumonia, pulmonary sarcoidosis, silicosis, pulmonary fibrosis, respiratory failure, acute respiratory distress syndrome, emphysema, chronic bronchitis, tuberculosis, lung cancer, or a chronic respiratory condition. In certain embodiments, the deuterium-enriched compound is administered by oral administration.

Another aspect of the invention provides a method of achieving an effect selected from the group consisting of: (a) reducing the amount of a triglyceride or low-density lipoprotein (LDL) in a patient, and (b) increasing the amount of high-density lipoprotein (HDL) in a patient. The method comprises administering to a patient in need thereof an effective amount of a deuterium-enriched compound described herein, such as a compound of Formula I or Formula II, having an optical purity of at least 75% enantiomeric excess to achieve said effect. In certain embodiments, the deuterium-enriched compound is a compound of Formula I. In certain other embodiments, the deuterium-enriched compound is a compound of Formula II.

Another aspect of the invention provides a method of treating an inflammatory or immune-mediated disorder selected from the group consisting chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, rhinitis, and a dermatological condition. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II. In yet other embodiments, the inflammatory or immune-mediated disorder is further selected from an inflammatory condition that contributes to metabolic syndrome.

Another aspect of the invention provides a method of treating a dermatological disorder selected from the group consisting of psoriasis, atopic dermatitis, acne, leukoplakia, scleroderma, and a skin malignancy. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Another aspect of the invention provides a method of achieving an effect selected from the group consisting of: (a) modulating expression of a pro-inflammatory cytokine (e.g., TNFα, IL-1β, or IL-6) in a patient suffering from an inflammatory disorder, (b) modulating expression of an anti-inflammatory cytokine in a patient suffering from an inflammatory disorder, (c) modulating macrophage function in a patient suffering from an infection, and (d) modulating stem cell differentiation in a patient. The method comprises administering to a patient in need thereof an effective amount of a deuterium-enriched compound described herein, such as a compound of Formula I or Formula II, having an optical purity of at least 75% enantiomeric excess to achieve said effect. In certain embodiments, the deuterium-enriched compound is a compound of Formula I. In certain other embodiments, the deuterium-enriched compound is a compound of Formula II.

Another aspect of the invention provides a method of promoting wound healing. The method comprises administering to a patient in need thereof a therapeutically effective amount of a deuterium-enriched compound described herein, such as a compound of Formula I or Formula II, having an optical purity of at least 75% enantiomeric excess to promote wound healing. In certain embodiments, the deuterium-enriched compound is a compound of Formula I. In certain other embodiments, the deuterium-enriched compound is a compound of Formula II.

Another aspect of the invention provides a method of treating a disorder selected from the group consisting of transplant rejection liver functional impairment, Rabson-Mendenhall syndrome, Donohue syndrome, Leber hereditary optic neuropathy, myotonic dystrophy, ototoxicity, Niemann Pick disease, autosomal dominant optic atrophy, spinal bulbar muscular atrophy, Mohr-Tranebjaerg syndrome, hereditary spastic paraplegia, MELAS syndrome, monoclonal immunoglobulin deposition disease (MIDD), deafness, insulin resistance in a patient receiving growth hormone, and chronic progressive external ophthalmoplegia with mitochondrial myopathy. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

DETAILED DESCRIPTION

Figure 1:
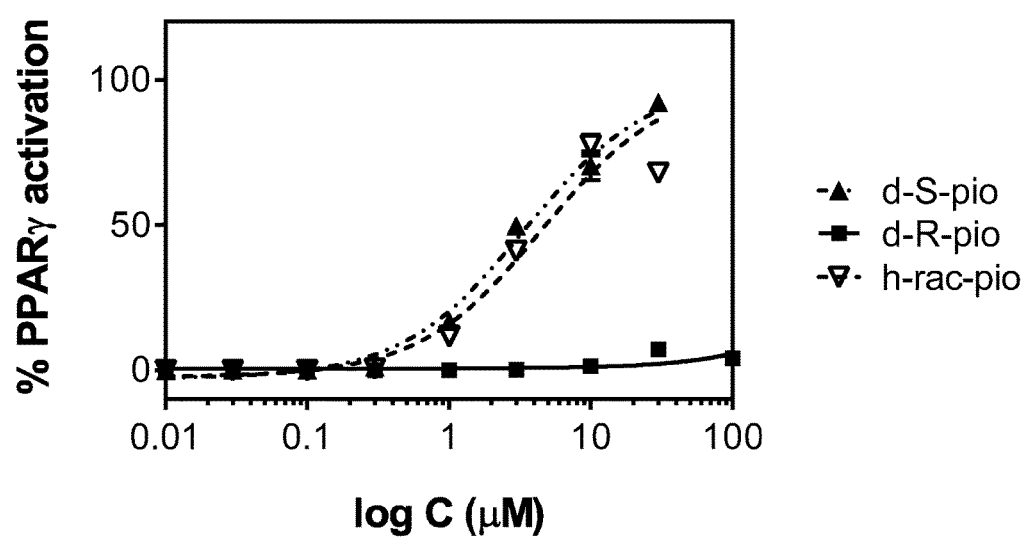
FIG. 1 is a line graph depicting results of PPARγ agonist activity testing for d-S-pio, d-R-pio, and h-rac-pio, as further described in Example 3.

The invention provides enantiopure deuterium-enriched pioglitazone, pharmaceutical compositions, and methods of treating neurological disorders, cancer, respiratory disorders, metabolic disorders, and other disorders using enantiopure deuterium-enriched pioglitazone. Deuterium-enriched refers to the feature that the compound has a quantity of deuterium that is greater than in naturally occurring compounds or synthetic compounds prepared from substrates having the naturally occurring distribution of isotopes. The threshold amount of deuterium enrichment is specified in certain instances in this disclosure, and all percentages given for the amount of deuterium present are mole percentages.

Deuterium ($^2$H) is a stable, non-radioactive isotope of $^1$H hydrogen and has an atomic weight of 2.014. Hydrogen naturally occurs as a mixture of the isotopes $^1$H hydrogen (i.e., protium), deuterium ($^2$H), and tritium ($^3$H). The natural abundance of deuterium is 0.015%. One of ordinary skill in the art recognizes that in all chemical compounds with an H atom, the H atom actually represents a mixture of $^1$H hydrogen, deuterium ($^2$H), and tritium ($^3$H), where about 0.015% is deuterium. Thus, compounds with a level of deuterium that has been enriched to be greater than its natural abundance of 0.015% are considered unnatural and, as a result, novel over their non-enriched counterparts.

The deuterium-enriched pioglitazone described herein contains deuterium enrichment at the chiral center of pioglitazone and optionally in other locations in the compound. Deuterium-enrichment at the chiral center reduces the rate at which the two enantiomers of pioglitazone may interconvert. Further, the deuterium-enriched pioglitazone described herein is provided in enantiomerically pure form. This enantiomerically pure, deuterium-enriched pioglitazone provides for a better therapeutic agent than non-deuterated pioglitazone and/or racemic mixtures of the compound.

Exemplary compositions and methods of the present invention are described in more detail in the following sections: I. Deuterium-enriched Pioglitazone; II. Therapeutic Applications; III. Dosing Considerations and Combination Therapy, and IV. Pharmaceutical Compositions. Aspects of the invention described in one particular section are not to be limited to any particular section.

I. Deuterium-Enriched Pioglitazone

One aspect of the invention provides deuterium-enriched compounds for use in the therapeutic methods and pharmaceutical compositions described herein. The deuterium-enriched compounds are provided in high enantiomeric purity in order to maximize therapeutic benefit, such as maximal potency per dose of therapeutic agent and minimize adverse side effects.

One such deuterium-enriched compound is a family of deuterium-enriched compounds represented by Formula I having an optical purity of at least 75% enantiomeric excess:

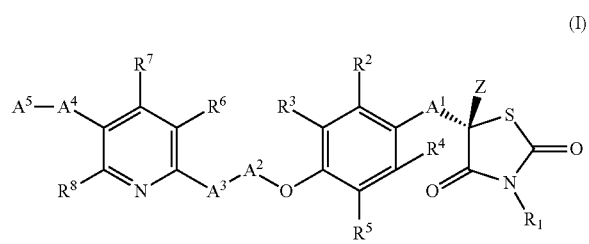

(I)

or a pharmaceutically acceptable salt thereof, wherein:
$A^1$, $A^2$, $A^3$, and $A^4$ are independently —C($R^9$)($R^{10}$)—;
$A^5$ is —C($R^{11}$)($R^{12}$)($R^{13}$);
$R^1$, $R^2$, $R^3$, $R^4$, $R^5$, $R^6$, $R^7$, and $R^8$ are independently H or D;
$R^9$, $R^{10}$, $R^{11}$, $R^{12}$, and $R^{13}$ each represent independently for each occurrence H or D; and
Z is H or D, provided that the abundance of deuterium in Z is at least 30%.

In certain embodiments, $A^1$ is —CH$_2$—. In certain embodiments, $A^2$ is —CH$_2$—. In certain embodiments, $A^3$ is —CH$_2$—. In certain embodiments, $A^4$ is —CH$_2$—. In certain embodiments, $A^2$ and $A^3$ are —CH$_2$—. In certain other embodiments, $A^1$, $A^2$, $A^3$, and $A^4$ are —CH$_2$—.

In certain embodiments, $A^5$ is —CH$_3$. In certain embodiments, $A^4$ is —CH$_2$—, and $A^5$ is —CH$_3$.

In certain embodiments, $R^1$ is H. In certain embodiments, $R^2$ is H. In certain embodiments, $R^3$ is H. In certain embodiments, $R^4$ is H. In certain embodiments, $R^5$ is H. In certain embodiments, $R^6$ is H. In certain embodiments, $R^2$ is H. In certain embodiments, $R^8$ is H. In certain other embodiments, $R^1$, $R^2$, $R^3$, $R^4$, $R^5$, $R^6$, $R^7$, and $R^8$ are H.

The description above describes multiple embodiments relating to compounds of Formula I. The patent application specifically contemplates all combinations of the embodiments. For example, the invention contemplates a compound of Formula I wherein $R^1$, $R^2$, $R^3$, $R^4$, $R^5$, $R^6$, $R^7$, and $R^8$ are H; $A^1$, $A^2$, $A^3$, and $A^4$ are —CH$_2$—; and $A^5$ is —CH$_3$.

Another such deuterium-enriched compound is a family of deuterium-enriched compounds represented by Formula I-A having an optical purity of at least 75% enantiomeric excess:

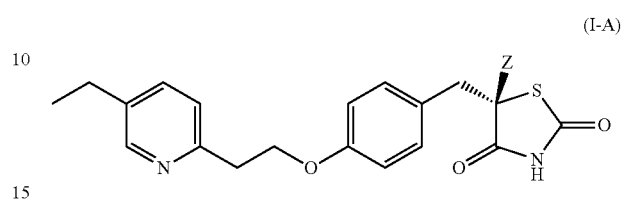

(I-A)

or a pharmaceutically acceptable salt thereof, wherein Z is H or D, provided that the abundance of deuterium in Z is at least 30%.

The compounds of Formula I and Formula I-A can be further characterized according to the abundance of deuterium at the position defined by variable Z. In certain embodiments, the abundance of deuterium in Z is selected from: (a) at least 40%, (b) at least 50%, (c) at least 60%, (d) at least 70%, (e) at least 75%, (f) at least 80%, (g) at least 90%, (h) at least 95%, (h) at least 97%, and (i) about 100%. Additional examples of the abundance of deuterium in Z include 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

In certain embodiments, the abundance of deuterium in Z is at least 60%. In certain other embodiments, the abundance of deuterium in Z is at least 75%. In yet other embodiments, the abundance of deuterium in Z is at least 90%.

The compounds of Formula I and Formula I-A can be further characterized according their enantiomeric purity. In certain embodiments, the deuterium-enriched compound has an enantiomeric excess of at least 80%, 85%, 90%, 95%, or 98%. Still further examples of the optical purity include an enantiomeric excess of at least 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

Still further such deuterium-enriched compounds are provided in Tables 1 and 2 below.

TABLE 1

| Compound No. | Structure |
|---|---|
| 1 | 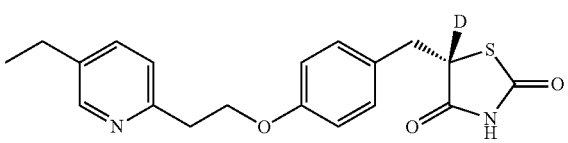 [SMILES: [2H][C@@]1(Cc2ccc(OCCc3ccc(CC)cn3)cc2)SC(=O)NC1=O] | or a pharmaceutically acceptable salt thereof, each having an optical purity of at least 60% enantiomeric excess.

| 2 | (same structure) | having an optical purity of at least 60% enantiomeric excess.

TABLE 1-continued

| Compound No. | Structure |
|---|---|
| 3 | (5-ethylpyridin-2-yl)ethoxy-phenyl thiazolidinedione structure with D label<br>hydrochloride having an optical purity of at least 60% enantiomeric excess. |
| 4 | (5-ethylpyridin-2-yl)ethoxy-phenyl thiazolidinedione structure with D label<br>or a pharmaceutically acceptable salt thereof, each having an optical purity of at least 75% enantiomeric excess. |
| 5 | (5-ethylpyridin-2-yl)ethoxy-phenyl thiazolidinedione structure with D label<br>having an optical purity of at least 75% enantiomeric excess. |
| 6 | (5-ethylpyridin-2-yl)ethoxy-phenyl thiazolidinedione structure with D label<br>hydrochloride having an optical purity of at least 75% enantiomeric excess. |
| 7 | (5-ethylpyridin-2-yl)ethoxy-phenyl thiazolidinedione structure with D label<br>or a pharmaceutically acceptable salt thereof, each having an optical purity of at least 90% enantiomeric excess. |
| 8 | (5-ethylpyridin-2-yl)ethoxy-phenyl thiazolidinedione structure with D label<br>having an optical purity of at least 90% enantiomeric excess. |
| 9 | (5-ethylpyridin-2-yl)ethoxy-phenyl thiazolidinedione structure with D label<br>hydrochloride having an optical purity of at least 90% enantiomeric excess. |
| 10 | (5-ethylpyridin-2-yl)ethoxy-phenyl thiazolidinedione structure with D label<br>or a pharmaceutically acceptable salt thereof, each having an optical purity of at least 95% enantiomeric excess. |

TABLE 1-continued

| Compound No. | Structure |
|---|---|
| 11 | 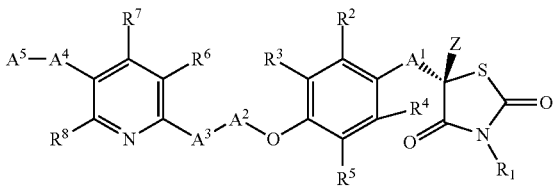
having an optical purity of at least 95% enantiomeric excess. |
| 12 | (structure shown) hydrochloride having an optical purity of at least 95% enantiomeric excess. |

TABLE 2

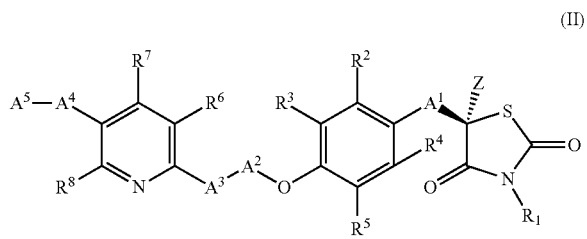

| Compound No. | Variable Definition |
|---|---|
| 1 | Z = D; $R^1$ = D; $R^2$-$R^8$ are H; $A^1$, $A^2$, $A^3$, and $A^4$ are —CH$_2$—; and $A^5$ is —CH$_3$ |
| 2 | Z = D; $R^1$-$R^8$ are H; $A^1$ = —CD$_2$—; $A^2$, $A^3$, and $A^4$ are —CH$_2$—; and $A^5$ is —CH$_3$ |
| 3 | Z = D; $R^1$ = H; $R^2$, $R^3$, $R^4$, and $R^5$ are D; $R^6$-$R^8$ are H; $A^1$, $A^2$, $A^3$, and $A^4$ are —CH$_2$—; and $A^5$ is —CH$_3$ |
| 4 | Z = D; $R^1$-$R^8$ are H; $A^1$ = —CH$_2$—; $A^2$ and $A^3$ are —CD$_2$—; $A^4$ = —CH$_2$—; and $A^5$ is —CH$_3$ |
| 5 | Z = D; $R^1$, $R^2$, $R^3$, $R^4$, and $R^5$ are H; $R^6$-$R^8$ are D; $A^1$, $A^2$, $A^3$, and $A^4$ are —CH$_2$—; and $A^5$ is —CH$_3$ |
| 6 | Z = D; $R^1$-$R^8$ are H; $A^1$, $A^2$, and $A^3$ are —CH$_2$—; $A^4$ are —CD$_2$—; and $A^5$ is —CD$_3$ |

Another embodiment of the invention provides a compound in Table 2 wherein the compound has an enantiomeric excess of at least 60%, 70%, 75%, 80%, 85%, 90%, 95%, or 98%.

Another such deuterium-enriched compound is a family of deuterium-enriched compounds represented by Formula II having an optical purity of at least 75% enantiomeric excess:

(II)

or a pharmaceutically acceptable salt thereof, wherein:
$A^1$, $A^2$, $A^3$, and $A^4$ are independently —C($R^9$)($R^{10}$)—;
$A^5$ is —C($R^{11}$)($R^{12}$)($R^{13}$);

$R^1$, $R^2$, $R^3$, $R^4$, $R^5$, $R^6$, $R^7$, and $R^8$ are independently H or D;

$R^9$, $R^{10}$, $R^{11}$, $R^{12}$, and $R^{13}$ each represent independently for each occurrence H or D; and Z is H or D, provided that the abundance of deuterium in Z is at least 30%.

In certain embodiments, $A^1$ is —CH$_2$—. In certain embodiments, $A^2$ is —CH$_2$—. In certain embodiments, $A^3$ is —CH$_2$—. In certain embodiments, $A^4$ is —CH$_2$—. In certain embodiments, $A^2$ and $A^3$ are —CH$_2$—. In certain other embodiments, $A^1$, $A^2$, $A^3$, and $A^4$ are —CH$_2$—.

In certain embodiments, $A^5$ is —CH$_3$. In certain embodiments, $A^4$ is —CH$_2$—, and $A^5$ is —CH$_3$.

In certain embodiments, $R^1$ is H. In certain embodiments, $R^2$ is H. In certain embodiments, $R^3$ is H. In certain embodiments, $R^4$ is H. In certain embodiments, $R^5$ is H. In certain embodiments, $R^6$ is H. In certain embodiments, $R^7$ is H. In certain embodiments, $R^8$ is H. In certain other embodiments, $R^1$, $R^2$, $R^3$, $R^4$, $R^5$, $R^6$, $R^7$, and $R^8$ are H.

The description above describes multiple embodiments relating to compounds of Formula II. The patent application specifically contemplates all combinations of the embodiments. For example, the invention contemplates a compound of Formula II wherein $R^1$, $R^2$, $R^3$, $R^4$, $R^5$, $R^6$, $R^7$, and $R^8$ are H; $A^1$, $A^2$, $A^3$, and $A^4$ are —CH$_2$—; and $A^5$ is —CH$_3$.

Another such deuterium-enriched compound is a family of deuterium-enriched compounds represented by Formula II-A having an optical purity of at least 75% enantiomeric excess:

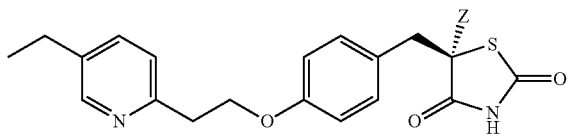 [SMILES: [2H][C@]1(Cc2ccc(OCCc3ccc(CC)cn3)cc2)SC(=O)NC1=O]

(II-A)

or a pharmaceutically acceptable salt thereof, wherein Z is H or D, provided that the abundance of deuterium in Z is at least 30%.

The compounds of Formula II and Formula II-A can be further characterized according to the abundance of deuterium at the position defined by variable Z. In certain embodiments, the abundance of deuterium in Z is selected from: (a) at least 40%, (b) at least 50%, (c) at least 60%, (d) at least 70%, (e) at least 75%, (f) at least 80%, (g) at least 90%, (h) at least 95%, (h) at least 97%, and (i) about 100%. Additional examples of the abundance of deuterium in Z include 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

In certain embodiments, the abundance of deuterium in Z is at least 60%. In certain other embodiments, the abundance of deuterium in Z is at least 75%. In yet other embodiments, the abundance of deuterium in Z is at least 90%.

The compounds of Formula II and Formula II-A can be further characterized according their enantiomeric purity. In certain embodiments, the deuterium-enriched compound has an enantiomeric excess of at least 80%, 85%, 90%, 95%, or 98%. Still further examples of the optical purity include an enantiomeric excess of at least 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

Still further such deuterium-enriched compounds are provided in Tables 3 and 4 below.

TABLE 3

| Compound No. | Structure |
|---|---|
| 1 | ![structure] <br> or a pharmaceutically acceptable salt thereof, each having an optical purity of at least 60% enantiomeric excess. |
| 2 | ![structure] <br> having an optical purity of at least 60% enantiomeric excess. |
| 3 | ![structure] <br> hydrochloride having an optical purity of at least 60% enantiomeric excess. |
| 4 | ![structure] <br> or a pharmaceutically acceptable salt thereof, each having an optical purity of at least 75% enantiomeric excess |
| 5 | ![structure] <br> having an optical purity of at least 75% enantiomeric excess. |

TABLE 3-continued

| Compound No. | Structure |
|---|---|
| 6 | [Structure: 5-ethylpyridine connected via ethyl-O-phenyl-CH2 to thiazolidine-2,4-dione with D label] hydrochloride having an optical purity of at least 75% enantiomeric excess. |
| 7 | [Structure: 5-ethylpyridine connected via ethyl-O-phenyl-CH2 to thiazolidine-2,4-dione with D label] or a pharmaceutically acceptable salt thereof, each having an optical purity of at least 90% enantiomeric excess. |
| 8 | [Structure: 5-ethylpyridine connected via ethyl-O-phenyl-CH2 to thiazolidine-2,4-dione with D label] having an optical purity of at least 90% enantiomeric excess. |
| 9 | [Structure: 5-ethylpyridine connected via ethyl-O-phenyl-CH2 to thiazolidine-2,4-dione with D label] hydrochloride having an optical purity of at least 90% enantiomeric excess. |
| 10 | [Structure: 5-ethylpyridine connected via ethyl-O-phenyl-CH2 to thiazolidine-2,4-dione with D label] or a pharmaceutically acceptable salt thereof, each having an optical purity of at least 95% enantiomeric excess. |
| 11 | [Structure: 5-ethylpyridine connected via ethyl-O-phenyl-CH2 to thiazolidine-2,4-dione with D label] having an optical purity of at least 95% enantiomeric excess. |
| 12 | [Structure: 5-ethylpyridine connected via ethyl-O-phenyl-CH2 to thiazolidine-2,4-dione with D label] hydrochloride having an optical purity of at least 95% enantiomeric excess. |

TABLE 4

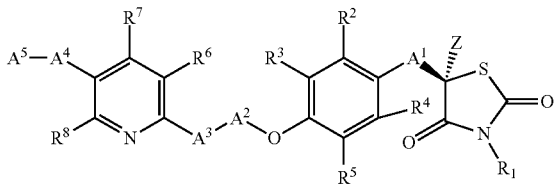

Compound
No.  Variable Definition

1  Z = D; R$^1$ = D; R$^2$-R$^8$ are H; A$^1$, A$^2$, A$^3$, and A$^4$ are —CH$_2$—; and A$^5$ is —CH$_3$
2  Z = D; R$^1$-R$^8$ are H; A$^1$ = —CD$_2$—; A$^2$, A$^3$, and A$^4$ are —CH$_2$—; and A$^5$ is —CH$_3$
3  Z = D; R$^1$ = H; R$^2$, R$^3$, R$^4$, and R$^5$ are D; R$^6$-R$^8$ are H; A$^1$, A$^2$, A$^3$, and A$^4$ are —CH$_2$—; and A$^5$ is —CH$_3$
4  Z = D; R$^1$-R$^8$ are H; A$^1$ = —CH$_2$—; A$^2$ and A$^3$ are —CD$_2$—; A$^4$ = —CH$_2$—; and A$^5$ is —CH$_3$
5  Z = D; R$^1$, R$^2$, R$^3$, R$^4$, and R$^5$ are H; R$^6$-R$^8$ are D; A$^1$, A$^2$, A$^3$, and A$^4$ are —CH$_2$—; and A$^5$ is —CH$_3$
6  Z = D; R$^1$-R$^8$ are H; A$^1$, A$^2$, and A$^3$ are —CH$_2$—; A$^4$ are —CD$_2$—; and A$^5$ is —CD$_3$ Another embodiment of the invention provides a compound in Table 4 wherein the compound has an enantiomeric excess of at least 60%, 70%, 75%, 80%, 85%, 90%, 95%, or 98%.

As indicated above, the deuterium-enriched compound may be in the form of a pharmaceutically acceptable salt. One such pharmaceutically acceptable salt is a hydrochloride salt.

It is understood that the deuterium-enriched compounds described herein can be combined with a pharmaceutically acceptable carrier to form a pharmaceutical composition.

Deuterium-enriched compounds of the invention can generally be prepared by substituting a deuterium-enriched reagent for a non-isotopically labeled reagent in synthetic schemes reported in the literature for making non-isotopically labeled pioglitazone. Scheme 1 below illustrates a general method for preparing deuterium-enriched pioglitazone, in which deuterium is incorporated at the sole chiral center. The scheme is provided for the purpose of illustrating the invention, and should not be regarded in any manner as limiting the scope or the spirit of the invention. In Scheme 1, pioglitazone hydrochloride is first stirred with perdeuterated dimethylsulfoxide (d$_6$-DMSO) and triethylamine and then treated with perdeuterated methanol (d$_4$-MeOH). The R-enantiomer and S-enantiomer of deutero-amine A are separated using chiral chromatography, such as chiral high-performance liquid chromatography. Alternatively, the R-enantiomer and S-enantiomer of deutero-amine A may be separated by reaction with a chiral carboxylic acid to form a salt, followed by separation of the resulting diastereomeric salts, and conversion of the separated salts back to deuterated pioglitazone free base in enantio-pure form. Pioglitazone hydrochloride can be prepared using the methods described in for example, U.S. Pat. No. 4,444,779; EP 193256; U.S. Pat. Nos. 4,687,777; 8,173,816; and U.S. Patent Application Publication No. 2011/0021576, each of which is incorporated herein by reference.

Scheme 1.

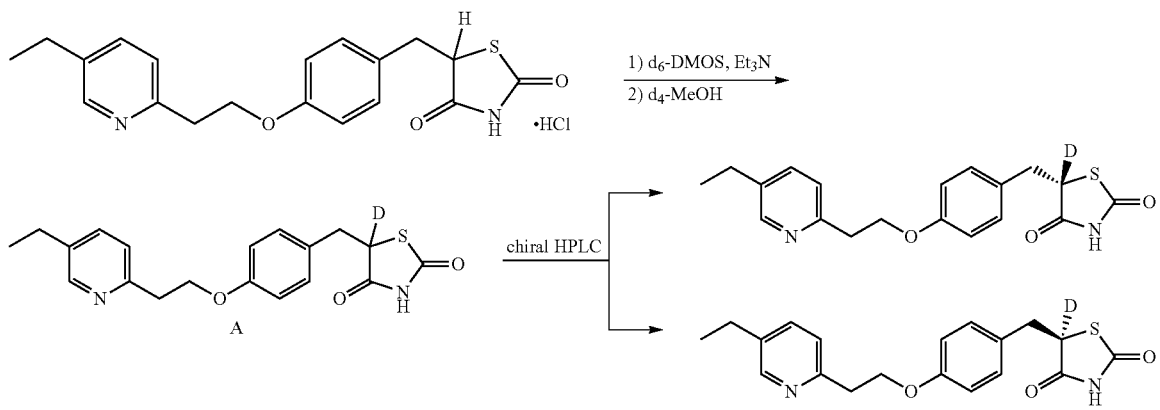

Scheme 2 below illustrates a general method for preparing deuterium-enriched pioglitazone, in which deuterium is incorporated at the ethyl group attached to the pyridine and at the sole chiral center. Reaction of 2-(5-(d$_5$-ethyl)pyridin-2-yl)ethanol (A1) with p-fluoro-nitrobenzene provides nitrophenyl ether B1. Reduction of nitrophenyl ether B1, such as through hydrogenation in the presence of palladium/carbon, provides aminophenyl ether C1. Reaction of aminophenyl ether C1 with NaNO$_2$ and hydrobromic acid, followed by addition of CH$_2$=CHCO$_2$Et provides alpha-bromo ester D1. Reaction of alpha-bromo ester D1 with thiourea provides thiazolidine-2,4-dione E1. Reaction of thiazolidine-2,4-dione E1 with d$_6$-DMSO and triethylamine, followed by d$_4$-MeOH provides deutero-thiazolidine-2,4-dione F1. The R-enantiomer and S-enantiomer of deutero-thiazolidine-2,4-dione F1 are separated using chiral chromatography, such as chiral high-performance liquid chromatography.

Another aspect of the invention provides a unit quantum of a deuterium-enriched compound described herein, such as an amount of at least (a) one µg of a disclosed deuterium-enriched compound, (b) one mg, or (c) one gram. In further embodiments, the quantum is, for example, at least 0.01,

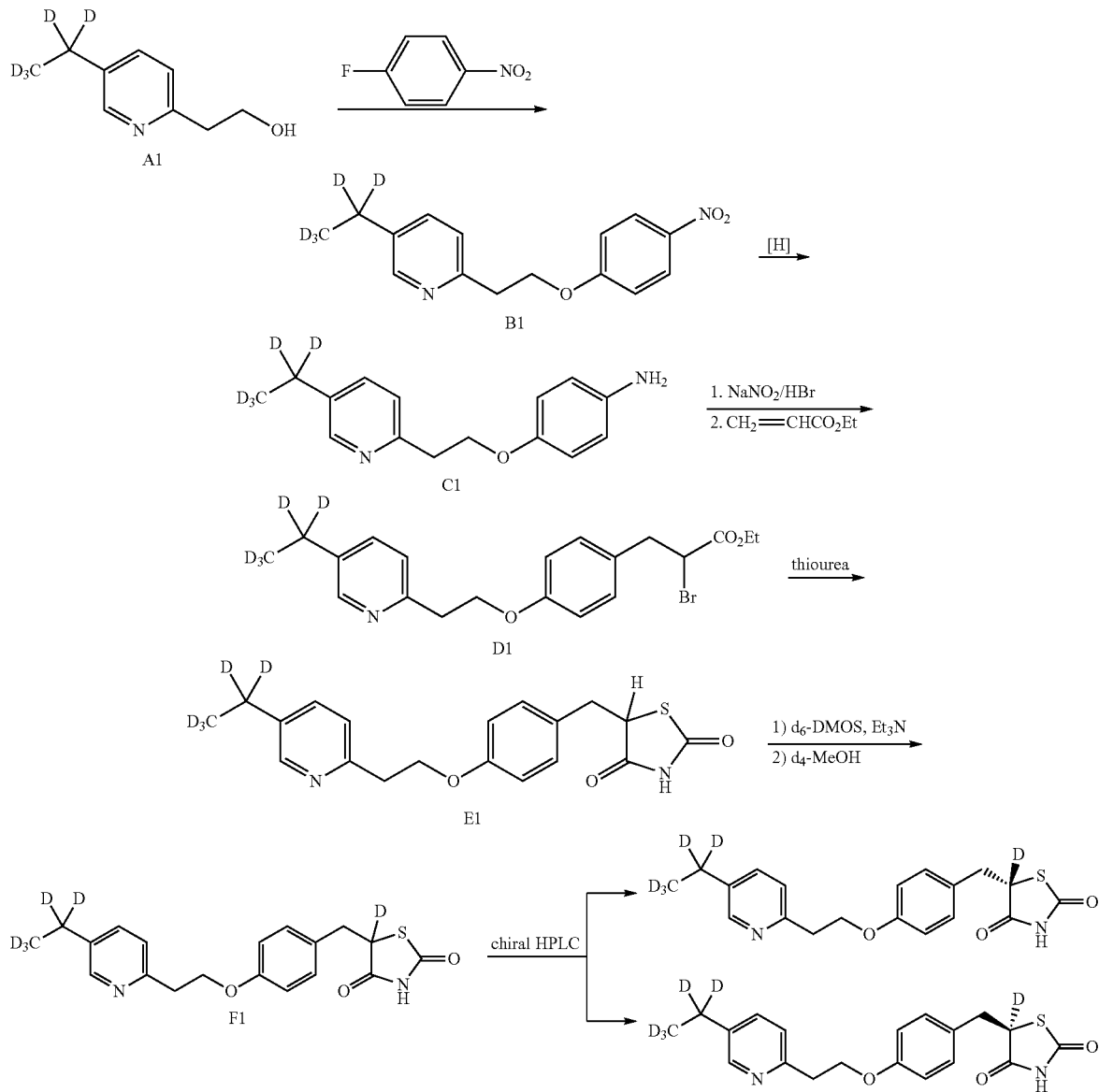

Compounds having deuterium enrichment at a position other than the ethyl group on the pyridine can be prepared using other deuterated forms of starting materials shown in Scheme 2 (e.g., a deuterated form of p-fluoro-nitrobenzene).

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, to 100% by weight.

0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

II. Therapeutic Applications

The invention provides methods of using deuterium-enriched compounds described herein to treat medical disorders. Preferred medical disorders for treatment include neurological disorders, cancer, respiratory disorders, and metabolic disorders. Use of the deuterium-enriched compounds having high enantiomeric purity is contemplated to maximize therapeutic benefit, such as achieving increased potency per dose of therapeutic agent and minimize adverse side effects. The deuterium-enriched compound can be, for example, a compound of Formula I, Formula I-A, Formula II, Formula II-A, or one of the other deuterium-enriched compounds described in Section I above.

Treating Neurological Disorders

Accordingly, one aspect of the invention provides a method of treating a neurological disorder selected from the group consisting of Alzheimer's disease, Parkinson's disease, amyotrophic lateral sclerosis, Friedreich's ataxia, autism spectrum disorder, depression, mild cognitive impairment, Down syndrome, neurodegeneration, adrenoleukodystrophy, Huntington's disease, stroke, traumatic brain injury, substance abuse, spinal cord injury, neuronal injury, major depression or bipolar disorder comorbid with metabolic syndrome, and a neurological disorder caused by functional mitochondrial impairment. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II. In certain embodiments, the neurological disorder is selected from the group consisting of Alzheimer's disease, Parkinson's disease, amyotrophic lateral sclerosis, Friedreich's ataxia, autism spectrum disorder, depression, mild cognitive impairment, neurodegeneration, adrenoleukodystrophy, Huntington's disease, stroke, traumatic brain injury, substance abuse, spinal cord injury, neuronal injury, and major depression or bipolar disorder comorbid with metabolic syndrome. In certain embodiments, the neurological disorder is selected from the group consisting of Alzheimer's disease, Parkinson's disease, amyotrophic lateral sclerosis, Friedreich's ataxia, depression, mild cognitive impairment, neurodegeneration, adrenoleukodystrophy, and Huntington's disease. In certain other embodiments, the neurological disorder is Alzheimer's disease. In certain other embodiments, the neurological disorder is Down syndrome.

In certain other embodiments, the neurological disorder is a cognitive disorder, such as cognitive impairment and/or memory impairment. The cognitive impairment may be, for example, cognitive impairment associated with Alzheimer's disease.

In certain embodiments, the substance abuse is one or more of alcohol craving, heroin dependence, and nicotine dependence.

Treating Cancer

Another aspect of the invention provides a method of treating cancer. The method comprises administering to a patient in need thereof a therapeutically effective amount of a deuterium-enriched compound described herein, such as a compound of Formula I or Formula II, having an optical purity of at least 75% enantiomeric excess to treat the cancer. In certain embodiments, the deuterium-enriched compound is a compound of Formula I. In certain other embodiments, the deuterium-enriched compound is a compound of Formula II.

In certain embodiments, the cancer is lung cancer, hepatocellular carcinoma, astrocytoma, glioma, glioblastoma, meningioma, liver cancer, lymphoma, melanoma, multiple myeloma, pancreatic cancer, colorectal cancer, pituitary cancer, thyroid cancer, esophageal cancer, or prostate cancer. In certain embodiments, the cancer is non-small cell lung cancer or hepatocellular carcinoma.

In certain other embodiments, the cancer is lung cancer, hepatocellular carcinoma, astrocytoma, glioma, glioblastoma, meningioma, liver cancer, lymphoma, melanoma, multiple myeloma, pancreatic cancer, colorectal cancer, pituitary cancer, thyroid cancer, esophageal cancer, prostate cancer, ear cancer, nose cancer, throat cancer, kidney cancer, breast cancer, stomach cancer, or uterine cancer. In certain other embodiments, the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratosis, acute lymphocytic leukemia, acute myeloid leukemia, adenoid cystic carcinoma, adenoma, adenosarcoma, adenosquamous carcinoma, anal canal cancer, anal cancer, anorectal cancer, astrocytic tumor, Bartholin's gland carcinoma, basal cell carcinoma, biliary cancer, bone cancer, bone marrow cancer, bronchial cancer, bronchial gland carcinoma, carcinoid, cholangiocarcinoma, chorioid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastoma, hemangioendothelioma, hemangioma, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanoma, lymphoma, male genital cancer, malignant melanoma, malignant mesothelial tumor, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma, nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumor, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T-cell leukemia, tongue cancer, undifferentiated carcinoma, ureter cancer, urethral cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

Treating Respiratory Disorders

Another aspect of the invention provides a method of treating a respiratory disorder. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound described herein having the (S)-stereochemical configuration at the stereocenter of the thiazolidine-2,4-dione ring. In certain embodiments, the deuterium-enriched compound is a compound of Formula I. In certain other embodiments, the deuterium-enriched compound is a compound of Formula II.

In certain embodiments, the deuterium-enriched compound is administered by pulmonary administration. In a more specific embodiment, the deuterium-enriched compound is a compound described herein having the (S)-stereochemical configuration at the stereocenter of the thiazolidine-2,4-dione ring, and said compound is administered by pulmonary administration. In another more specific embodiment, the deuterium-enriched compound is a compound of Formula I and said compound is administered by pulmonary administration.

In certain embodiments, the deuterium-enriched compound is administered by routes other than pulmonary administration. In certain embodiments, the deuterium-enriched compound is administered by oral administration, sublingual administration, sublabial administration, rectal administration, injection, or transdermal administration. In certain embodiments, the deuterium-enriched compound is a compound of Formula I. In certain other embodiments, the deuterium-enriched compound is a compound of Formula II.

In certain embodiments, the respiratory disorder is chronic obstructive pulmonary disease, asthma, bronchitis, cystic fibrosis, pulmonary edema, pulmonary embolism, pulmonary arterial hypertension, pneumonia, pulmonary sarcoidosis, silicosis, pulmonary fibrosis, respiratory failure, acute respiratory distress syndrome, emphysema, chronic bronchitis, tuberculosis, lung cancer, or a chronic respiratory condition. In certain embodiments, the respiratory disorder is chronic obstructive pulmonary disease, asthma, or a chronic respiratory condition. In certain other embodiments, the respiratory disorder is chronic obstructive pulmonary disease. In yet other embodiments, the respiratory disorder is bronchitis, cystic fibrosis, pulmonary edema, pulmonary embolism, pneumonia, pulmonary sarcoidosis, silicosis, pulmonary fibrosis, respiratory failure, acute respiratory distress syndrome, emphysema, chronic bronchitis, tuberculosis, or lung cancer. In certain embodiments, the asthma is mild asthma, moderate asthma, severe asthma, or steroid-resistant asthma.

Treating Metabolic Disorders

Another aspect of the invention provides a method of treating a metabolic disorder selected from the group consisting of non-alcoholic fatty liver disease, viral hepatitis, liver cirrhosis, liver fibrosis, diabetic retinopathy, diabetic neuropathy, diabetic nephropathy, beta cell depletion insulin resistance in a patient with congenital adrenal hyperplasia treated with a glucocorticoid, dysmetabolism in peritoneal dialysis patients, reduced insulin secretion, improper distribution of brown fat cells and white fat cells, obesity, or improper modulation of leptin levels. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II. In certain embodiments, the metabolic disorder is further selected from a complication of diabetes. In certain embodiments, the metabolic disorder is non-alcoholic fatty liver disease, diabetic retinopathy, diabetic neuropathy, diabetic nephropathy, or beta cell depletion insulin resistance in a patient with congenital adrenal hyperplasia treated with a glucocorticoid. In certain embodiments, the metabolic disorder is non-alcoholic fatty liver disease, diabetic retinopathy, diabetic neuropathy, diabetic nephropathy, beta cell depletion, reduced insulin secretion, improper distribution of brown fat cells and white fat cells, obesity, or improper modulation of leptin levels. In certain other embodiments, the metabolic disorder is non-alcoholic fatty liver disease. In certain other embodiments, the metabolic disorder is beta cell loss treatable by B-cell regeneration. In certain other embodiments, the metabolic disorder is central obesity, dyslipidemia, or pre-diabetes.

Treating a Symptom of Hepatitis

Another aspect of the invention provides a method of treating a symptom of hepatitis. The method comprises administering to a patient in need thereof a therapeutically effective amount of a deuterium-enriched compound described herein, such as a compound of Formula I or Formula II, having an optical purity of at least 75% enantiomeric excess to treat a symptom of hepatitis. In certain embodiments, the deuterium-enriched compound is a compound of Formula I. In certain other embodiments, the deuterium-enriched compound is a compound of Formula II Treating Cardiovascular Disease Another aspect of the invention provides a method of treating a cardiovascular disease. The method comprises administering to a patient in need thereof a therapeutically effective amount of a deuterium-enriched compound described herein, such as a compound of Formula I or Formula II, having an optical purity of at least 75% enantiomeric excess to treat the cardiovascular disease. In certain embodiments, the deuterium-enriched compound is a compound of Formula I. In certain other embodiments, the deuterium-enriched compound is a compound of Formula II. In certain embodiments, the cardiovascular disease is hypertension, hyperlipidemia, atherosclerosis, improper vascular function, dyslipidemia, stenosis, restenosis, myocardial infarction, stroke, intracranial hemorrhage, acute coronary syndrome, stable angina pectoris, or unstable angina pectoris. In certain other embodiments, the cardiovascular disorder is intracranial hemorrhage, acute coronary syndrome, stable angina pectoris, or unstable angina pectoris.

In another aspect, the invention provides a method for preventing stroke in a patient. The method comprises administering to a patient in need thereof a therapeutically effective amount of a deuterium-enriched compound described herein, such as a compound of Formula I or Formula II, having an optical purity of at least 75% enantiomeric excess to prevent said stroke.

The method of treatment or the method of prevention may involve a patient at risk for central nervous system ischemic stroke, or may involve a patient at risk for stroke due to cardiovascular disease.

Reducing the Amount of a Triglyceride or Low-Density Lipoprotein

Another aspect of the invention provides a method of reducing the amount of a triglyceride or low-density lipoprotein (LDL) in a patient. The method comprises administering to a patient in need thereof an effective amount of a deuterium-enriched compound described herein, such as a compound of Formula I or Formula II, having an optical purity of at least 75% enantiomeric excess to reduce the amount of a triglyceride or LDL in the patient. In certain embodiments, the deuterium-enriched compound is a compound of Formula I. In certain other embodiments, the deuterium-enriched compound is a compound of Formula II.

In certain embodiments, the method provides a reduction of at least 1%, 5%, 10%, or 25% in the amount of a triglyceride or low-density lipoprotein (LDL) in the patient.

Increasing the Amount of High-Density Lipoprotein

Another aspect of the invention provides a method of increasing the amount of high-density lipoprotein (HDL) in a patient. The method comprises administering to a patient in need thereof a therapeutically effective amount of a deuterium-enriched compound described herein, such as a compound of Formula I or Formula II, having an optical purity of at least 75% enantiomeric excess to increase the amount of HDL in the patient. In certain embodiments, the deuterium-enriched compound is a compound of Formula I. In certain other embodiments, the deuterium-enriched compound is a compound of Formula II.

In certain embodiments, the method provides an increase of at least 1%, 5%, 10%, or 25% in the amount of high-density lipoprotein (HDL) in a patient.

Treating an Inflamatory or Immune-Mediated Disorder

Another aspect of the invention provides a method of treating an inflammatory or immune-mediated disorder selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, rhinitis (e.g., allergic rhinitis), and a dermatological condition. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II. In certain embodiments, the inflammatory or immune-mediated disorder is selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, and a dermatological condition. In certain embodiments, the inflammatory or immune-mediated disorder is selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, and a dermatological condition, in certain embodiments, the chronic kidney disease may be, for example, polycystic kidney disease (such as autosomal dominant or autosomal recessive).

Treating a Dermatological Disorder

Another aspect of the invention provides a method of treating a dermatological disorder selected from the group consisting of psoriasis, atopic dermatitis, acne, leukoplakia, scleroderma, and a skin malignancy. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Modulating Expression of Pro-Inflammatory Cytokines

Another aspect of the invention provides a method of modulating expression of a pro-inflammatory cytokine (e.g., TNFα, IL-1β, or IL-6) in a patient suffering from an inflammatory disorder. The method comprises administering to a patient in need thereof an effective amount of a deuterium-enriched compound described herein, such as a compound of Formula I or Formula II, having an optical purity of at least 75% enantiomeric excess to modulate expression of the pro-inflammatory cytokine. In certain embodiments, the pro-inflammatory cytokine is TNFα. In certain embodiments, the deuterium-enriched compound is a compound of Formula I. In certain other embodiments, the deuterium-enriched compound is a compound of Formula II.

Another aspect of the invention provides a method of modulating expression of an anti-inflammatory cytokine in a patient suffering from an inflammatory disorder. The method comprises administering to a patient in need thereof an effective amount of a deuterium-enriched compound described herein, such as a compound of Formula I or Formula II, having an optical purity of at least 75% enantiomeric excess to modulate expression of the anti-inflammatory cytokine. In certain embodiments, the deuterium-enriched compound is a compound of Formula I. In certain other embodiments, the deuterium-enriched compound is a compound of Formula II.

Modulating Macrophage Function

Another aspect of the invention provides a method of modulating macrophage function in a patient suffering from an infection. The method comprises administering to a patient in need thereof an effective amount of a deuterium-enriched compound described herein, such as a compound of Formula I or Formula II, having an optical purity of at least 75% enantiomeric excess to modulate macrophage function. In certain embodiments, the deuterium-enriched compound is a compound of Formula I. In certain other embodiments, the deuterium-enriched compound is a compound of Formula II.

Method of Promoting Wound Healing

Another aspect of the invention provides a method of promoting wound healing. The method comprises administering to a patient in need thereof a therapeutically effective amount of a deuterium-enriched compound described herein, such as a compound of Formula I or Formula II, having an optical purity of at least 75% enantiomeric excess to promote wound healing. In certain embodiments, the deuterium-enriched compound is a compound of Formula I. In certain other embodiments, the deuterium-enriched compound is a compound of Formula II.

Treating Skin Defects

Another aspect of the invention provides a method of treating skin defects caused by exposure to ultraviolet radiation. The method comprises administering to a patient in need thereof a therapeutically effective amount of a deuterium-enriched compound described herein, such as a compound of Formula I or Formula II, having an optical purity of at least 75% enantiomeric excess to treat skin defects caused by exposure to ultraviolet radiation. In certain embodiments, the deuterium-enriched compound is a compound of Formula I. In certain other embodiments, the deuterium-enriched compound is a compound of Formula II.

Method of Modulating Stem Cell Differentiation

Another aspect of the invention provides a method of modulating stem cell differentiation, such as in a patient. The method comprises exposing a stem cell to a deuterium-enriched compound described herein, such as a compound of Formula I or Formula II, having an optical purity of at least 75% enantiomeric excess to modulate stem cell differentiation. In certain embodiments, the deuterium-enriched compound is a compound of Formula I. In certain other embodiments, the deuterium-enriched compound is a compound of Formula II. In certain embodiments, the method modulates stem cell differentiation in a patient by administering to the patient an effective amount of a compound herein, such as a compound of Formula I or Formula II, having an optical purity of at least 75% enantiomeric excess.

Additional Medical Disorders

Another aspect of the invention provides a method of treating a disorder selected from the group consisting of transplant rejection, liver functional impairment, Rabson-Mendenhall syndrome, Donohue syndrome, Leber hereditary optic neuropathy, myotonic dystrophy, ototoxicity, Niemann Pick disease, autosomal dominant optic atrophy, spinal bulbar muscular atrophy, Mohr-Tranebjaerg syndrome, hereditary spastic paraplegia, MELAS syndrome, monoclonal immunoglobulin deposition disease (MIDD), deafness, insulin resistance in a patient receiving growth hormone, and chronic progressive external ophthalmoplegia with mitochondrial myopathy. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Preventing Medical Disorders

Also provided are methods of preventing a medical disorder in a patient. The method comprises administering to a patient in need thereof an effective amount of a deuterium-enriched compound described herein, such as a compound of Formula I or Formula II, having an optical purity of at least 75% enantiomeric excess to prevent the medical disorder. The medical disorder may be one or more of the medical disorders recited above, such as a neurological disorder (e.g., Alzheimer's disease or Parkinson's disease), cancer (e.g., non-small cell lung cancer or hepatocellular carcinoma), a metabolic disorder, a cardiovascular disorder (e.g. in-stent renarrowing in diabetes patients, reinfarction in diabetes patients, or cardiac allograft vasculopathy after heart transplant), or a respiratory disorder (e.g., chronic obstructive pulmonary disease).

Additional Medical Uses

Also provided are methods of using compounds herein for therapy comprising regenerative medicine. Also provided are methods of treating veterinary disorders, such as laminitis, using a compound described herein, such as a compound of Formula I or Formula II, having an optical purity of at least 75% enantiomeric excess to treat the veterinary disorder.

Manufacture of Medicaments

Another aspect of the invention provides for the use of a deuterium-enriched compound described herein in the manufacture of a medicament. The medicament may be for treating one or more of the medical disorders described herein, such as treating a neurological disorder (e.g., Alzheimer's disease or Parkinson's disease), cancer (e.g., non-small cell lung cancer or hepatocellular carcinoma), a metabolic disorder, or a respiratory disorder (e.g., chronic obstructive pulmonary disease).

III. Dosing Considerations and Combination Therapy

Doses of a compound provided herein, or a pharmaceutically acceptable salt thereof, vary depending on factors such as: specific indication to be treated; age and condition of a patient; and amount of second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to about 500 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

In yet other embodiments, the daily dose can be from about 1 mg to 5 mg, 5 mg to 10 mg, 10 mg to 20 mg, 20 mg to 35 mg, 35 mg to 50 mg, 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, or 475 mg to 500 mg. In certain embodiments, the daily dosage is in the range of about 1 mg to 50 mg, 50 mg to 100 mg, 100 mg to 150 mg, 150 mg to 200 mg, 200 mg to 250 mg, 250 mg to 300 mg, 300 mg to 350 mg, 350 mg to 400 mg, or 400 mg to 500 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg.

Unless indicated otherwise, compounds described herein may be administered using any medically accepted route of administration. For example, in certain embodiments, unless indicated otherwise, the compound is administered by oral administration, injection, or transdermal administration. In a preferred embodiment, the compound is administered orally.

In certain aspects, the therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies. These regimens can avoid or reduce the side effects of one of the therapies, and/or improve the efficacy of the treatment.

Consequently, in another aspect, a compound provided herein is administered daily in a single or divided doses in a four to six week cycle with a rest period of about a week or two weeks. Cycling therapy further allows the frequency, number, and length of dosing cycles to be increased. Thus, another aspect encompasses the administration of a compound provided herein for more cycles than are typical when it is administered alone. In yet another aspect, a compound provided herein is administered for a greater number of cycles than would typically cause dose-limiting toxicity in a patient to whom a second active ingredient is not also being administered.

In another aspect, a compound provided herein is administered daily and continuously for three or four weeks at a dose of from about 0.1 mg to about 500 mg per day, followed by a rest of one or two weeks. In other embodiments, the dose can be from about 1 mg to about 500 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In another aspect, a compound provided herein and a second active ingredient are administered orally or parenterally, with administration of the compound provided herein occurring prior to (e.g., about 30 to 60 minutes) the second active ingredient, during a cycle of four to six weeks. In certain embodiments, the compound and second active agent are administered as a single dosage or they are administered separately. In another aspect, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about three to about four cycles.

Combination Therapy

A compound provided herein, or a pharmaceutically acceptable salt thereof, can be combined with other pharmacologically active compounds ("second active agents") in methods and compositions provided herein. Certain combinations may work synergistically in the treatment of particular types of diseases or disorders, and conditions and symptoms associated with such diseases or disorders. A compound provided herein, or a pharmaceutically acceptable salt thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

In certain embodiments, the combination therapy comprises a deuterium-enriched compound described herein and a second therapeutic agent for treating a metabolic disorder, such as metformin, a dipeptidyl peptidase IV inhibitor (e.g., sitagliptin, vildagliptin, or the like), a statin (e.g., a HMG-CoA reductase inhibitor, such as atorvastatin, cerivastatin, fluvastatin, lovastatin, mevastatin, simvastatin, rosuvastatin, pravastatin, or combination thereof), a GLP-1 agonist, a GLP-2 agonist, or an SGLT2 inhibitor. As appreciated, the combination therapy may comprising more than two therapeutic agents, such as where a combination of a deuterium-enriched compound described herein and at least two of the aforementioned agents for treating a metabolic disorder are administered to the patient.

In certain other embodiments, the combination therapy comprises a deuterium-enriched compound described herein and a diuretic agent, such as hydrochlorothiazide.

In certain other embodiments, the combination therapy comprises a deuterium-enriched compound described herein and a second therapeutic agent for treating hypertension, diabetes, or an inflammatory disorder. The second therapeutic agent may be one that limits the activity of the renin-angiotensin system, such as an angiotensin converting enzyme inhibitor (e.g., an ACE inhibitor, such as ramipril, captopril, enalapril, or the like), an angiotensin receptor blocker (e.g., candesartan, losartan, olmesartan, or the like), or a renin inhibitor. Alternatively, the second therapeutic agent may limit hypertension by alternate means, such as a beta-adrenergic receptor blocker or calcium channel blocker (e.g., amlodipine).

In certain other embodiments, the combination therapy comprises a deuterium-enriched compound described herein and a glucocorticoid agonist. Such combination therapy may be particularly useful for treating an inflammatory disorder, such as therapy for suppressing an immune response, preventing transplant rejection, and treating autoimmune disease. Exemplary disorders include, for example, rheumatoid arthritis, lupus, myasthenia gravis, muscular dystrophy vasculitis, multiple sclerosis, chronic obstructive pulmonary disease (COPD), inflammatory bowel disease, treatment of acute allergic reactions, and transplant rejection. In certain other embodiments, the combination therapy comprises a deuterium-enriched compound described herein and a second therapeutic agent for treating a kidney disease. Exemplary such second therapeutic agents include those that increase cAMP or comprise a beta-adrenergic agonist. Exemplary beta-adrenergic agonists include, for example, a beta-1-adrenergic agonist, a beta-2-adrenergic agonist, a beta-3-adrenergic agonist, or a combination thereof. In certain embodiments, the second therapeutic agent is noradrenaline, isoprenaline, dobutamine, salbutamol, levosalbutamol, terbutaline, pirbuterol, procaterol, metaproterenol, fenoterol, bitolterol mesylate, salmeterol, formoterol, bambuterol, clenbuterol, indacaterol, L-796568, amibegron, solabegron, isoproterenol, albuterol, metaproterenol, arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, prenalterol, ractopamine, reproterol, rimiterol, ritodrine, tretoquinol, tulobuterol, xamoterol, zilpaterol, zinterol, or a pharmaceutically acceptable salt thereof; or a combination of any of the foregoing.

In certain other embodiments, the combination therapy comprises a deuterium-enriched compound described herein and a second therapeutic agent for treating cancer. Exemplary second therapeutic agents for treating cancer include, for example, an alkylating agent, an anti-metabolite (i.e., a molecule that impedes DNA and/or RNA synthesis), an anti-microtubule agent, a topoisomerase inhibitor, a cytotoxic antibiotic, a tyrosine kinase inhibitor, an inhibitor of tumor necrosis factor alpha, anti-neoplastic radiation therapy, or a Programmed Death protein-1 (PD-1) modulator (e.g., an inhibitor). In certain embodiments, the second therapeutic agent for treating cancer is azacitidine, azathioprine, bleomycin, carboplatin, capecitabine, carmustine, cisplatin, chlorambucil, cyclophosphamide, cytarabine, dacarbazine, daunorubicin, docetaxel, doxifluridine, doxorubicin, epirubicin, epothilone, etoposide, fluorouracil, fulvestrant, gemcitabine, hydroxyurea, idarubicin, imatinib, lomustine, mechlorethamine, mercaptopurine, methotrexate, mitoxantrone, oxaliplatin, paclitaxel, pemetrexed, procarbazine, raloxifene, teniposide, temozolomide, tamoxifen, toremifene, valrubicin, vinblastine, vincristine, vindesine, vinorelbine, or a pharmaceutically acceptable salt thereof.

In yet other embodiments, the second therapeutic agent for treating cancer is abraxane; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate: bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol: celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; de/.aguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatm; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegasparagase; peliomycin; pentamustine; peplomycin sulfate; perfosfamide; pipobroman; piposulfan; piroxantrone hydrochloride; plicamycin; plomestane; porfimer sodium; portiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; a stem cell treatment; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; or zorubicin hydrochloride.

Administration of a compound provided herein, or a pharmaceutically acceptable salt thereof, and the second active agent(s) to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One route of administration for compounds provided herein is oral. Routes of administration for the second active agents or ingredients are known to those of ordinary skill in the art. See, e.g., Physicians' Desk Reference ($60^{th}$ Ed., 2006).

IV. Pharmaceutical Compositions

The invention provides pharmaceutical compositions comprising a deuterium-enriched compound described herein, such as a compound of Formula I or II, and a pharmaceutically acceptable carrier. In certain embodiments, the pharmaceutical compositions comprise a therapeutically-effective amount of a deuterium-enriched compound described herein, such as a compound of Formula I or II, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Pharmaceutical compositions can be used in the preparation of individual, single unit dosage forms. Pharmaceutical compositions and dosage forms provided herein comprise a compound provided herein, or a pharmaceutically acceptable salt thereof. Pharmaceutical compositions and dosage forms can further comprise one or more excipients. Additionally, pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., Remington's Pharmaceutical Sciences, 18th ed., Mack Publishing, Easton Pa. (1990).

The suitability of a particular excipient may depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose or other mono- or disaccharides. As used herein, the term "lactose-free" means that the amount of lactose present, if any, is insufficient to substantially increase the degradation rate of an active ingredient. Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients. Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are, in another aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In another aspect, dosage forms comprise a compound provided herein in an amount of from about 0.10 to about 500 mg. Examples of dosages include, but are not limited to, 0.1, 1, 2, 5, 7.5, 10, 12.5, 15, 17.5, 20, 25, 50, 100, 150, 200, 250, 300, 350, 400, 450, or 500 mg.

In another aspect, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In another aspect, the invention provides oral dosage forms that are tablets or capsules, in which case solid excipients are employed. In another aspect, the tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinylpyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in another aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In another aspect, pharmaceutical compositions comprise from about 0.5 to about 15 weight percent of disintegrant, or from about 1 to about 5 weight percent of disintegrant. Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a Syloid® silica gel (AEROSIL200, manufactured by W. R. Grace Co. of Baltimore, Md.), a coagulated aerosol of synthetic silica (marketed by Degussa Co. of Plano, Tex.), CAB-O-SIL® (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In another aspect, the invention provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008, 719, 5,674,533, 5,059,595, 5,591,767, 5,120,548, 5,073,543, 5,639,476, 5,354,556, and 5,733,566, each of which is incorporated in its entirety herein by reference. Such dosage forms can be used to provide slow or controlled-release of one or more active ingredients using, for example, hydroxypropyl methyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the invention provides single unit dosage forms suitable for oral administration such as, but not limited to, tablets, capsules, gel caps, and caplets that are adapted for controlled-release.

Parenteral dosage forms can be administered to patients by various routes including, but not limited to, subcutaneous, intravenous (including bolus injection), intramuscular, and intraarterial. Administration of a parenteral dosage form bypasses a patient's natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated in its entirety herein by reference.

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In another aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are nontoxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent. In other aspects, salts of the active ingredients can be used to further adjust the properties of the resulting composition.

In another aspect, the active ingredients provided herein are not administered to a patient at the same time or by the same route of administration. In another aspect, provided are kits which can simplify the administration of appropriate amounts of active ingredients.

In another aspect, the invention provides a kit comprising a dosage form of a compound provided herein. Kits can further comprise additional active ingredients or a pharmacologically active mutant or derivative thereof, or a combination thereof. Examples of the additional active ingredients include, but are not limited to, those disclosed herein.

In other aspects, the kits can further comprise devices that are used to administer the active ingredients. Examples of such devices include, but are not limited to, syringes, drip bags, patches, and inhalers.

V. Definitions

To facilitate an understanding of the present invention, a number of terms and phrases are defined below.

The term "compound" refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

Unless indicated otherwise, when a D is specifically recited at a position or is shown in a formula, this D represents a mixture of hydrogen and deuterium where the amount of deuterium is about 100% (i.e., the abundance of deuterium ranges from greater than 90% up to 100%). In certain embodiments, the abundance of deuterium in D is from 95% to 100%, or from 97% to 100%.

The term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

"Therapeutically effective amount" includes an amount of a compound of the invention that is effective when administered alone or in combination to treat the desired condition or disorder. "Therapeutically effective amount" includes an amount of the combination of compounds claimed that is effective to treat the desired condition or disorder. The combination of compounds can be additive and is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfuric, carbonic, citric, edetic, ethanedisulfonic, ethanesulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauric, lauryl sulfonic, maleic, malic, mandelic, methanesulfonic, napsylic, naphthylic, nitric, oleic, oxalic, palmitic, pamoic, pantothenic, phenylacetic, phosphoric, polygalacturonic, propionic, salicylic, stearic, succinic, sulfamic, sulfanilic, sulfuric, tannic, tartaric, toluenesulfonic, and valeric. (See, for example, Berge et al. (1977) "Pharmaceutical Salts", J. Pharm. Sci. 66:1-19.). In certain embodiments, the pharmaceutically acceptable salt is a hydrochloric acid salt.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or a water/oil emulsion), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, if a variable is not accompanied by a definition, then the previous definition of the variable controls.

Finally, the invention may be embodied in other specific forms without departing from the spirit or essential attributes thereof. This invention encompasses all combinations of aspects and embodiments of the invention noted herein. It is understood that any and all aspects of the invention may be taken in conjunction with any other aspects and/or embodiments to describe additional aspects. It is also to be understood that each individual element of the aspects is intended to be taken individually as its own independent aspect. Furthermore, any element of an aspect is meant to be combined with any and all other elements from any aspect to describe an additional aspect.

EXAMPLES

The invention now being generally described, will be more readily understood by reference to the following examples, which are included merely for purposes of illustration of certain aspects and embodiments of the present invention, and are not intended to limit the invention.

Example 1

Preparation of Racemic Deuterated Pioglitazone, (rac-5-({p-[2-(5-ethyl-2-pyridyl)ethoxy]phenyl}methyl)-(5-$^2$H)-1,3-thiazolidine-2,4-dione)

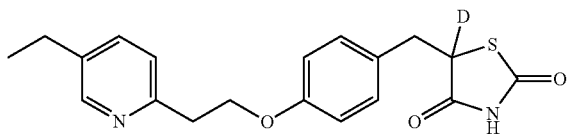 [SMILES: [2H]C1(Cc2ccc(OCCc3ccc(CC)cn3)cc2)SC(=O)NC1=O]

The hydrochloric acid salt of rac-5-({p-[2-(5-ethyl-2-pyridyl)ethoxy]phenyl}methyl)-1,3-thiazolidine-2,4-dione (i.e., pioglitazone hydrochloride) (1.5 g, 3.8 mmol) was placed in an oven-dried 250 mL round bottomed flask. Per-deuterated dimethylsulfoxide (d$_6$-DMSO, 18 mL) and triethylamine (1.596 mL, 11.5 mmol, 3 equiv.) were added, followed by per-deuterated methanol (d$_4$-MeOH, 14 mL). The resulting suspension was stirred at room temperature while monitoring by LC-MS. After 90 hours, d$_6$-DMSO (12 mL) and d$_4$-MeOH (16 mL) were added to dissolve the remaining solid. After another 18 hours (total 108 hours), LC-MS analysis showed almost complete deuterium incorporation with % D=98.3% at the chiral center. The mixture was concentrated under reduced pressure, then the concentrate was cooled to 0° C. and diluted with cold water (200 mL). The white solid that formed was filtered. The filtrate was extracted with ether (2×200 mL), and the organic layers were combined, dried over sodium sulfate (Na$_2$SO$_4$), and filtered. The white solid was combined with the filtrate. The solvent was evaporated under reduced pressure and the residue was dried overnight in vacuo to give 1.292 g (3.61 mmol) of rac-5-({p-[2-(5-ethyl-2-pyridyl)ethoxy]phenyl}methyl)-(5-$^2$H)-1,3-thiazolidine-2,4-dione as a white solid. Overall yield: 1.292 g (3.61 mmol, 95%), % D=98% at the chiral center.

Example 2

Isolation of Enantiopure (R)-Deuterated Pioglitazone and (S)-Deuterated Pioglitazone, ((5R)-5-({p-[2-(5-ethyl-2-pyridyl)ethoxy]phenyl}methyl)-(5-$^2$H)-1,3-thiazolidine-2,4-dione and (5S)-5-({p-[2-(5-ethyl-2-pyridyl)ethoxy]phenyl}methyl)-(5-$^2$H)-1,3-thiazolidine-2,4-dione)

rac-5-({p-[2-(5-Ethyl-2-pyridyl)ethoxy]phenyl}methyl)-(5-$^2$H)-1,3-thiazolidine-2,4-dione (413 mg, 1.155 mmol) was dissolved in 30 mL of acetonitrile and 2-propanol (1:1 v/v). Trifluoroacetic acid (TFA, 225 µL) was added and the enantiomers (2 mL per run) were separated by supercritical fluid chromatography using a ChiralPak AD-H column (21×250 mm) and a mobile phase of 30% acetonitrile:2-propanol (1:1 v/v) in carbon dioxide (CO$_2$). Peaks were detected by their UV signal at 254 nm. Fractions containing each enantiomer were pooled and evaporated. Purity and enantiomeric excess (% ee) were determined by supercritical fluid chromatography using an analytical ChiralPak AD-H column (4.6×100 mm) and the same mobile phase. Overall yield was 405.3 mg (1.134 mmol, 98%). The absolute configuration of each enantiomer was determined by measurement of its specific rotation in dioxane and then comparison with specific rotation data already published for the enantiomers of pioglitazone and deuterated pioglitazone (see International Patent Application Publication Nos. WO 2010/015818 and WO 2010/150014). Physical characterization data for each enantiomer is provided below.

(S)-5-({p-[2-(5-Ethyl-2-pyridyl)ethoxy]phenyl}methyl)-(5-$^2$H)-1,3-thiazolidine-2,4-dione (i.e., deuterated (S)-pioglitazone): 214.2 mg (0.599 mmol), 99.6% purity (UV, 220 nm), 99.0% ee; LC/MS: 358.26 (M+1) (>99% deuterium incorporation at the chiral center); $^1$H NMR (300 MHz, d$_6$-DMSO) δ (ppm): 8.34 (s, 1H), 7.55 (d, 1H, J=7.8 Hz), 7.25 (d, 1H, J=7.8 Hz), 7.11 (d, 2H, J=8.7 Hz), 6.84 (d, 2H, J=8.7 Hz), 4.29 (t, 2H, J=6.6 Hz), 3.28 (d, 1H, J=13.2 Hz), 3.12 (t, 2H, J=6.6 Hz), 3.03 (d, 1H, J=14.4 Hz), 2.58 (q, 2H, J=7.7 Hz), 1.16 (t, 3H, J=7.5 Hz); specific rotation [α]$_D$= −72.4° (c 0.5, 19° C., dioxane).

(R)-5-({p-[2-(5-Ethyl-2-pyridyl)ethoxy]phenyl}methyl)-(5-$^2$H)-1,3-thiazolidine-2,4-dione (i.e., deuterated (R)-pioglitazone): 191.1 mg (0.535 mmol), 100% purity (UV, 220 nm), 100% ee; LC/MS: 358.26 (M+1) (>99% deuterium incorporation at the chiral center); $^1$H NMR (300 MHz, d$_6$-DMSO) δ (ppm): 8.34 (s, 1H), 7.55 (d, 1H, J=7.8 Hz), 7.25 (d, 1H, J=7.8 Hz), 7.11 (d, 2H, J=8.7 Hz), 6.84 (d, 2H, J=8.7 Hz), 4.29 (t, 2H, J=6.6 Hz), 3.28 (d, 1H, J=13.2 Hz), 3.12 (t, 2H, J=6.6 Hz), 3.03 (d, 1H, J=14.4 Hz), 2.58 (q, 2H, J=7.7 Hz), 1.16 (t, 3H, J=7.5 Hz); specific rotation [α]=+94.3 (c 0.5, 19° C., dioxane).

Example 3

PPARγ Agonist Activity

Agonist activity of deuterated pioglitazone towards the peroxisome proliferator-activated receptor gamma (PPARγ) was evaluated in two separate experiments. Experimental procedures and results from the first experiment are provided in Part I below. Experimental procedures and results from the second experiment are provided in Part II below. A discussion of the results from each experiment are provided in Part III below.

Part I—Analysis of PPARγ Agonist Activity of (S)-5-({p-[2-(5-Ethyl-2-pyridyl)ethoxy]phenyl}methyl)-(5-$^2$H)-1,3-thiazolidine-2,4-dione (d-S-pio) and (R)-5-({p-[2-(5-Ethyl-2-pyridyl)ethoxy]phenyl}methyl)-(5-$^2$H)-1,3-thiazolidine-2,4-dione (d-R-pio)

Agonist activity of the enantiomers of 5-({p-[2-(5-ethyl-2-pyridyl)ethoxy]phenyl}methyl)-(5-$^2$H)-1,3-thiazolidine-2,4-dione at the peroxisome proliferator-activated receptor gamma (PPARγ) was evaluated in the thyroid receptor-associated protein complex, 220 kDa component (TRAP220) PPARγ coactivator recruitment assay performed at Cerep (France). Briefly, a mixture of labeled PPARγ and tagged TRAP220 coactivator was pre-incubated at room temperature for 30 minutes in the presence of a PPARγ-targeted fluorescence acceptor and test compound. A TRAP220-targeted fluorescence donor was then added and the mixture was incubated for 120 minutes at room temperature. Next, the fluorescence signal was measured and results expressed as a percent of control (10 μM rosiglitazone). A dose response curve was generated for each enantiomer and the experimental data was analyzed using the log(agonist) vs. response (three parameters) non-linear model in GraphPad Prism 6.0 (GraphPad Software, Inc., La Jolla, Calif.), with a fixed Hillslope of 1.

(S)-5-({p-[2-(5-Ethyl-2-pyridyl)ethoxy]phenyl}methyl)-(5-$^2$H)-1,3-thiazolidine-2,4-dione (i.e., deuterated (S)-pioglitazone) was the most potent ($EC_{50}$=707 nM) and gave the highest maximum coactivator recruitment (106%). (R)-5-({p-[2-(5-Ethyl-2-pyridyl)ethoxy] phenyl}methyl)-(5-$^2$H)-1,3-thiazolidine-2,4-dione (i.e., deuterated (R)-pioglitazone) was less potent ($EC_{50}$=4.4 μM) with only 29% maximum coactivator recruitment when compared to rosiglitazone.

Part II—Analysis of PPARγ Agonist Activity of rac-5-({p-[2-(5-Ethyl-2-pyridyl)ethoxy]phenyl}methyl)-1,3-thiazolidine-2,4-dione (h-rac-pio); (S)-5-({p-[2-(5-Ethyl-2-pyridyl)ethoxy]phenyl}methyl)-(5-$^2$H)-1,3-thiazolidine-2,4-dione (d-S-pio); and (R)-5-({p-[2-(5-Ethyl-2-pyridyl)ethoxy]phenyl}methyl)-(5-$^2$H)-1,3-thiazolidine-2,4-dione (d-R-pio)

PPARγ agonist activity of the following compounds was evaluated in the thyroid receptor-associated protein complex, 220 kDa component (TRAP220) PPARγ coactivator recruitement assay performed at Cerep (France):

rac-5-({p-[2-(5-Ethyl-2-pyridyl)ethoxy]phenyl}methyl)-1,3-thiazolidine-2,4-dione
(S)-5-({p-[2-(5-Ethyl-2-pyridyl)ethoxy]phenyl}methyl)-(5-$^2$H)-1,3-thiazolidine-2,4-dione
(R)-5-({p-[2-(5-Ethyl-2-pyridyl)ethoxy]phenyl}methyl)-(5-$^2$H)-1,3-thiazolidine-2,4-dione.

The experimental procedure involved subjecting a mixture of labeled PPARγ and tagged TRAP220 coactivator to pre-incubation with a fluorescence acceptor at room temperature for 30 minutes in the presence of the test compound. A fluorescence donor was then added, and the mixture was incubated for 120 minutes at room temperature. Next, the fluorescence signal was measured and results expressed as a percent of control (10 μM rosiglitazone). A dose response curve was generated for each enantiomer and the experimental data was analyzed using the log(agonist) vs. response (three parameters) non-linear model in GraphPad Prism 6.0 (GraphPad Software, Inc., La Jolla, Calif.), with a fixed Hillslope of 1 and maximum of 100%.

Experimental results are depicted in FIG. 1 and $EC_{50}$ values are provided in Table 5 below. d-S-pio was a more potent PPARγ agonist than h-rac-pio and d-R-pio. In this experiment, d-R-pio did not show any agonist activity at concentrations up to 100 μM.

TABLE 5

| Compound | $EC_{50}$ (μM) |
| --- | --- |
| d-S-pio | 3.47 |
| d-R-pio | >100 |
| h-rac-pio | 4.63 |

Part III—Discussion of PPARγ Agonist Activity Results from Parts I and II

Experimental results in Parts I and II illustrate the trend that d-S-pio is a much more potent agonist of PPARγ than d-R-pio. Differences in the specific $EC_{50}$ values from the experiment in Parts I and II are understood to reflect typical differences observed in such cell-based assays between separate executions of the experiments. Such differences do not significantly impact characterization of the relative difference in PPARγ agonist activity for compounds tested under the same execution of the experiment.

Example 4

Human and Mouse Plasma Stability Study of (S)-5-({p-[2-(5-ethyl-2-pyridyl)ethoxy]phenyl}methyl)-1,3-thiazolidine-2,4-dione; (R)-5-({p-[2-(5-ethyl-2-pyridyl)ethoxy]phenyl}methyl)-1,3-thiazolidine-2,4-dione; and rac-5-({p-[2-(5-ethyl-2-pyridyl)ethoxy]phenyl}methyl)-(5-$^2$H)-1,3-thiazolidine-2,4-dione rac-5-({p-[2-(5-Ethyl-2-pyridyl)ethoxy]phenyl}methyl)-(5-$^2$H)-1,3-thiazolidine-2,4-dione (d-rac-pio; a 1:1 mixture of (S)- and (R)-enantiomers 5-({p-[2-(5-ethyl-2-pyridyl)ethoxy]phenyl}methyl)-(5-$^2$H)-1,3-thiazolidine-2,4-dione) (d-rac-pio), (R)-5-({p-[2-(5-ethyl-2-pyridyl)ethoxy]phenyl}methyl)-1,3-thiazolidine-2,4-dione (h-R-pio), and (S)-5-({p-[2-(5-ethyl-2-pyridyl)ethoxy]phenyl}methyl)-1,3-thiazolidine-2,4-dione (h-S-pio) were dissolved in separate solutions of dimethylsulfoxide (DMSO). The stock solutions were diluted 1:49 v/v in C57BL/6 mouse or human plasma to 10, 5, and 5 μM concentrations for d-rac-pio, h-S-pio, and h-R-pio respectively. The plasma samples were incubated at 37° C. in duplicate (anticoagulant: K3EDTA). Aliquots (20 μL) were removed at t=0, 0.25, 0.5, 1, 2, 4, 8, 16, and 32 h, added to 130 μL acetonitrile, and vortexed. Samples were placed at −80° C. until the study was complete. After thawing, a 1:1 acetonitrile:water solution of internal standard (ISTD, $d_4$-pioglitazone, 1.6 μM) was added. The vortexed samples were centrifuged and 50 μL of supernatant was dispensed in a 96-well plate. These were further diluted with 200 μL of 0.1% acetic acid in water:acetonitrile 15:85 v/v.

The samples were analyzed semi-quantitatively by LC/MS-MS in MRM (multiple reaction monitoring) mode for concentrations of h-S-pio, h-R-pio, d-S-pio, and d-R-pio using a chiral column (ChiralPak IE-3, Chiral Technologies, West Chester, Pa.) for the separation of enantiomers (isocratic eluent: 01.% acetic acid in water/acetonitrile 15/85 v/v at 1 mL/min) All peak areas were normalized to the ISTD and peak areas for the deuterated enantiomers, d-S-pio and d-R-pio, were corrected for the isotopic peak of the corresponding protonated enantiomer, if present (an interference of 12.2% of the response for the protonated compound was determined experimentally). Corrected data were analyzed and plotted using Microsoft Excel 2013 (Microsoft Corp, Redmond, Wash.) and the Excel Solver as well as GraphPad Prism 6.0 (GraphPad Software LLC, La Jolla, Calif.) where appropriate.

Scheme 3 illustrates the possible reactions in a solution of deuterated racemic pioglitazone, where the abbreviations d-S, d-R, h-S, and h-R represent d-S-pio, d-R-pio, h-S-pio, and h-R-pio, respectively. The deuterium in both enantiomers, d-S and d-R, can be lost by D/H exchange to give both protonated enantiomers, h-S and h-R with rate constants $k_{DRR}$, $k_{DRS}$, $k_{DSR}$, and $k_{DSS}$. At the same time, the protonated enantiomers h-S and h-R can exchange with enantiomerization rate constants $k_{RS}$ and $k_{SR}$. All four compounds can also degrade with potentially different degradation rate constants $k_{dSd}$, $k_{dRd}$, $k_{hSd}$, and $k_{hRd}$.

Scheme 3.

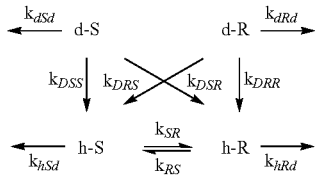

Human and mouse plasma data were analyzed independently. In addition, since the sum of peak areas for all enantiomeric isotopomers (h-S-pio+h-R-pio+d-S-pio+d-R-pio) appeared independent of incubation time in plasma from both species, degradation was considered negligible. Therefore, degradation rate constants $k_{hSd}$, $k_{hRd}$, $h_{dSd}$, and $k_{dRd}$ were set to 0. Data in each species was analyzed using a stepwise approach. Data for the enantiomerization reaction of h-S-pio and h-R-pio were fitted first and independently of each other. The average rate constants, $k_{SR}$ and $k_{RS}$, obtained from these analyses were used and fixed in the fitting of the stability data of d-rac-pio. Rate constants $k_{DSS}$, $k_{DSR}$, $k_{DRS}$, and $k_{DRR}$ were obtained from this final analysis. Half-lives for the 4 enantiomeric isotopomers were then calculated as $t_{1/2}=\ln(2)/k$, where $k=k_{DSR}+k_{DSS}$ or $k_{DRR}+k_{DRS}$ for the deuterated enantiomers (d-S-pio and d-R-pio, respectively) and $k=k_{SR}$ or $k_{RS}$ for the protonated enantiomers (h-S-pio and h-R-pio, respectively).

Data analysis was performed in Microsoft Excel 2013, using the Solver Generalized Reduced Gradient Nonlinear method with central derivatives to minimize the sum of sums of weighted $\Delta^2$, square of difference between ISTD-normalized experimental data and calculated value, divided by the experimental data (both protonated enantiomers or both protonated and deuterated enantiomers). Calculated concentrations were obtained through numerical approximation of differential equations (1) and (2) for the stability studies of h-S-pio and h-R-pio, and equations (3) to (6) for the stability study of d-rac-pio by the Euler method (equation (7)). The step between calculated time points was minimized in order to minimize the local error (proportional to the square of the step size) and the global error (proportional to the step size).

Figure 2A:
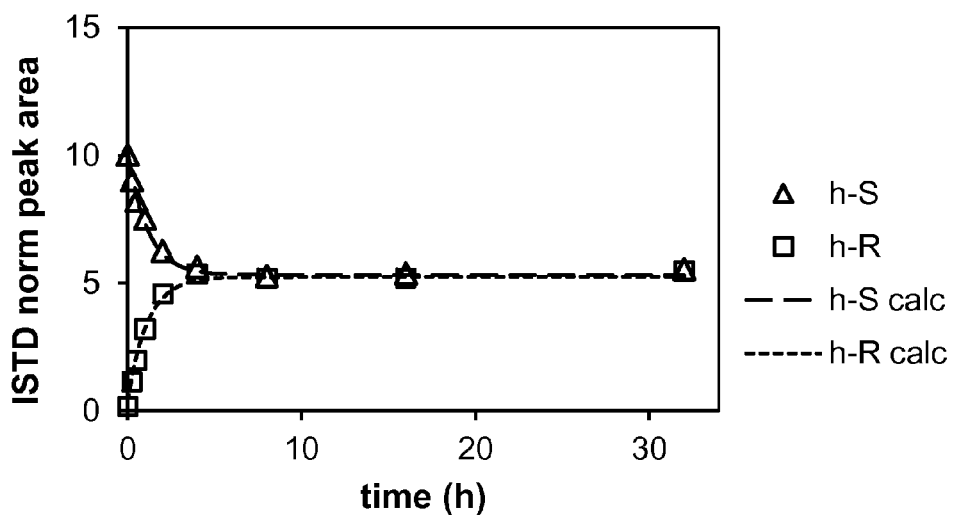
FIG. 2A is a line graph depicting in vitro stability data for h-S-pio in human plasma in the form of experimental data points and results from fitting to kinetic differential equations, as further described in Example 4. The abbreviation "calc" indicates results from fitting experimental data to kinetic differential equations.
Figure 2B:
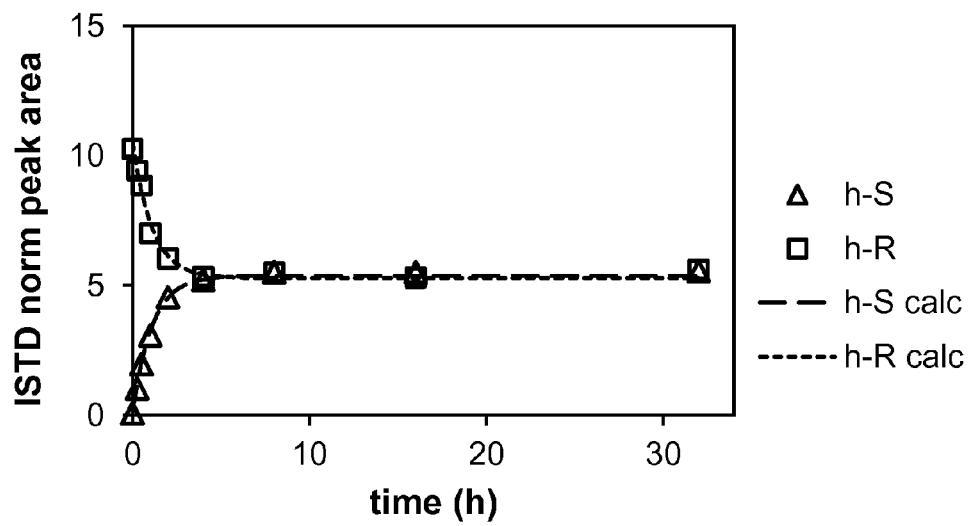
FIG. 2B is a line graph depicting in vitro stability data for h-R-pio in human plasma in the form of experimental data points and results from fitting to kinetic differential equations, as further described in Example 4. The abbreviation "calc" indicates results from fitting experimental data to kinetic differential equations.
Figure 2C:
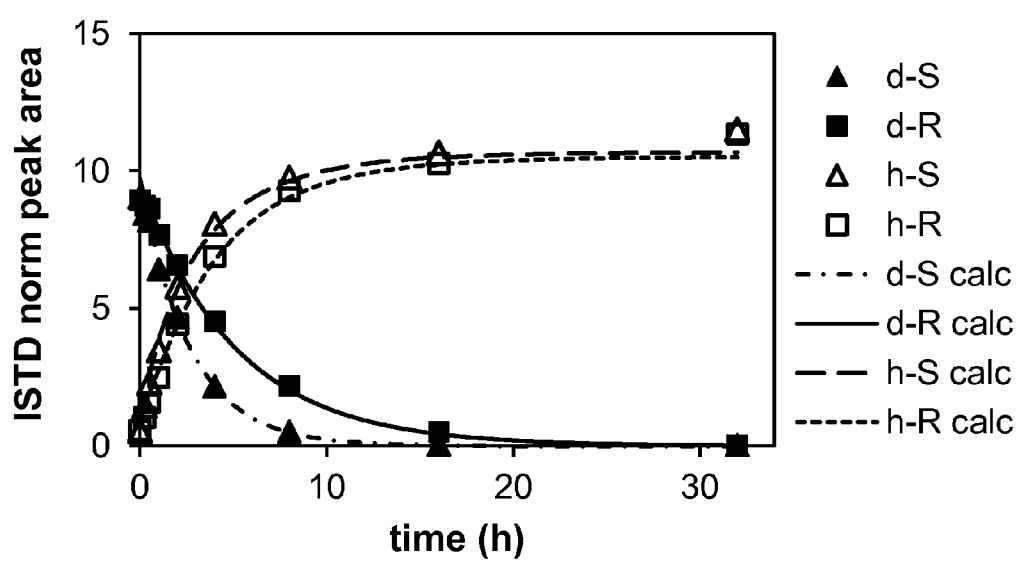
FIG. 2C is a line graph depicting in vitro stability data for d-rac-pio in human plasma in the form of experimental data points and results from fitting to kinetic differential equations, as further described in Example 4. The abbreviation "calc" indicates results from fitting experimental data to kinetic differential equations.
Figure 3A:
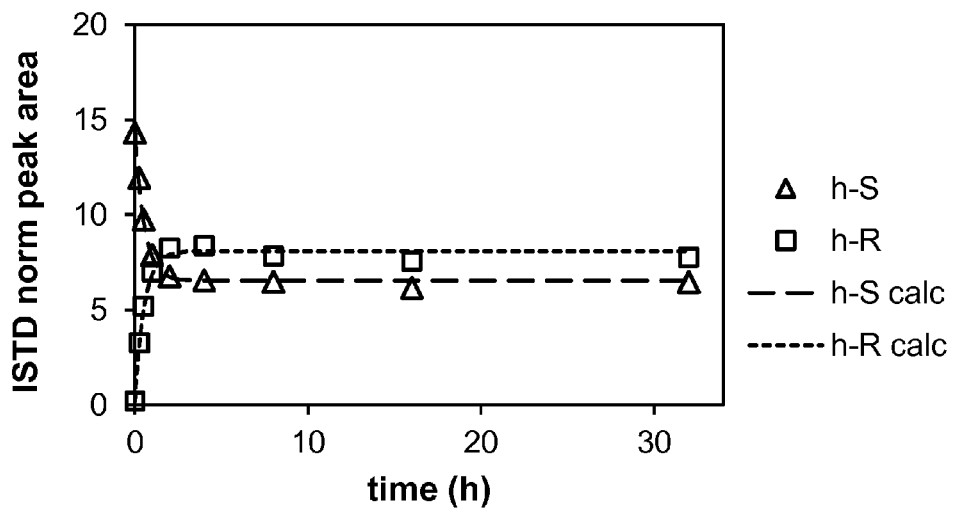
FIG. 3A is a line graph depicting in vitro stability data for h-S-pio in mouse plasma in the form of experimental data points and results from fitting to kinetic differential equations, as further described in Example 4. The abbreviation "calc" indicates results from fitting experimental data to kinetic differential equations.
Figure 3B:
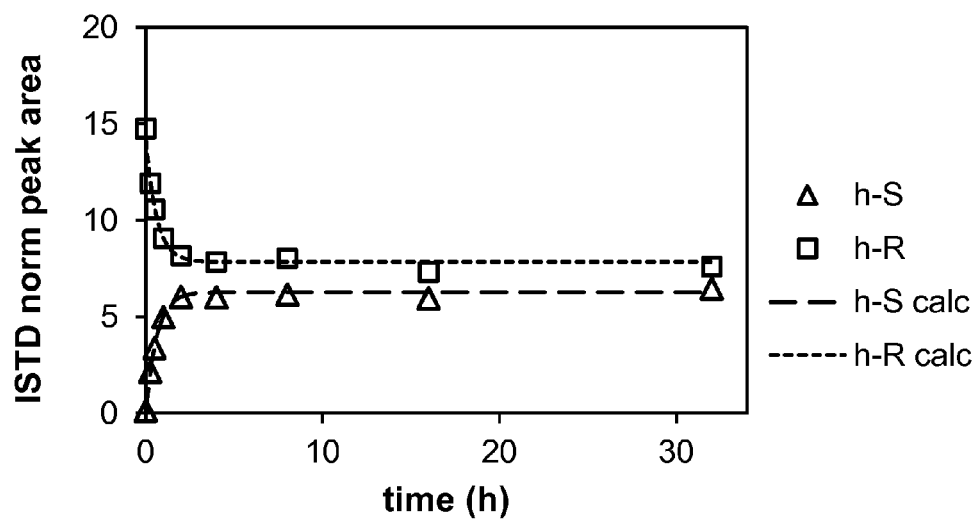
FIG. 3B is a line graph depicting in vitro stability data for h-R-pio in mouse plasma in the form of experimental data points and results from fitting to kinetic differential equations, as further described in Example 4. The abbreviation "calc" indicates results from fitting experimental data to kinetic differential equations.
Figure 3C:
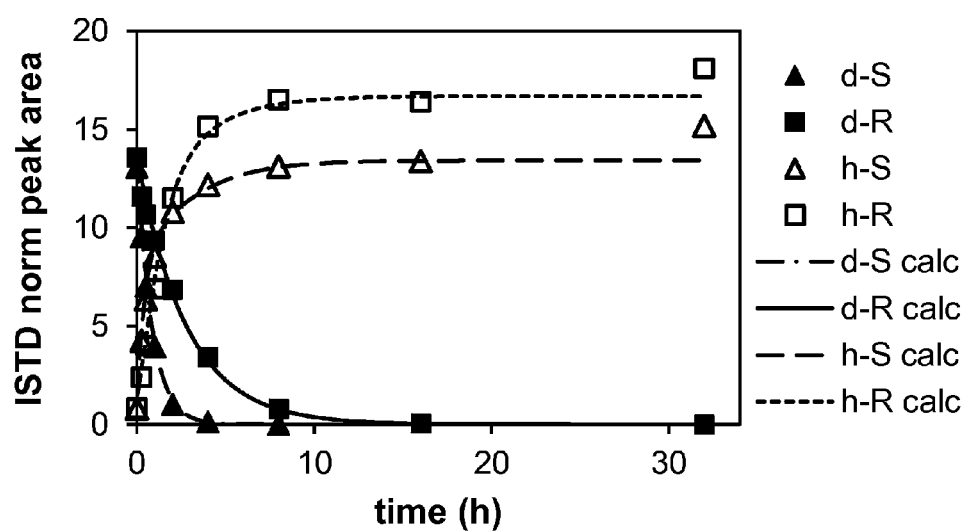
FIG. 3C is a line graph depicting in vitro stability data for d-rac-pio in mouse plasma in the form of experimental data points and results from fitting to kinetic differential equations, as further described in Example 4. The abbreviation "calc" indicates results from fitting experimental data to kinetic differential equations.

The observed and fitted data are shown in FIGS. 2A-C for stability in human plasma. The observed and fitted data are shown in FIGS. 3A-C for stability in mouse plasma. Fitted parameters are presented in Table 6, which provides rate constants and calculated half-lives ($t_{1/2}$) for the in vitro stability of h-S-pio, h-R-pio, and d-rac-pio in human and mouse plasma at 37° C. obtained by fitting experimental data to equations 1 to 6; the DXY stand for the D/H exchange reactions from d-S-pio (X=S) or d-R-pio (X=R) to h-S-pio (Y=S) or h-R-pio (Y=R); SR and RS represent the enantiomerization reaction h-S-pio to h-R-pio and h-R-pio to h-S-pio, respectively.

$$\frac{d[h-S]}{dt} = -k_{SR}[h-S] + k_{RS}[h-R]$$

$$\frac{d[h-R]}{dt} = k_{SR}[h-S] - k_{RS}[h-R]$$

$$\frac{d[h-S]}{dt} = -k_{SR}[h-S] + k_{RS}[h-R] + k_{DSS}[d-S] + k_{DRS}[d-R]$$

$$\frac{d[h-R]}{dt} = k_{SR}[h-S] - k_{RS}[h-R] + k_{DSR}[d-S] + k_{DRR}[d-R]$$

$$\frac{d[d-S]}{dt} = -(k_{DSS}+k_{DSR})[d-S]$$

$$\frac{d[d-R]}{dt} = -(k_{DRR}+k_{DRS})[d-R]$$

Equations 1-6 where [h-S], [h-R], [d-S], [d-R] are the concentrations of h-S-pio, h-R-pio, d-S-pio, and d-R-pio, respectively; $k_{SR}$ and $k_{RS}$ are the rate constants for the enantiomerization reactions h-S-pio to h-R-pio and h-R-pio to h-S-pio, respectively; $k_{DRR}$, $k_{DRS}$, $k_{DSR}$, and $k_{DSS}$ are the rate constants for the D/H exchange reactions d-S-pio or d-R-pio to h-S-pio or h-R-pio.

$$[X]_{t2}=[X]_{t1}+(t_2-t_1)[d[X]]_{t1}$$

Equation 7 where $[X]_{ti}$ is the concentration of h-S-pio, h-R-pio, d-S-pio or d-R-pio at time ti (wherein i=1 or 2, i.e., ti=t1 or t2), t1 is a time at which [X] is known, t2 is a time at which [X] is calculated, and $[d[X]]_{t1}$ is the calculated value of the differential equation at time t1.

The equilibrium ratio of enantiomers h-R/h-S was approximately 1:1 in human plasma. The equilibrium ratio of enantiomers h-R/h-S was approximately 1.25:1 in mouse plasma. The effect of deuterium incorporation was different for the two enantiomers. For example, an approximately two-fold increased half-life was observed for d-R-pio vs. h-R-pio. However, the half-life of d-S-pio was approximately the same as the half-life for h-S-pio.

TABLE 6

| Species | Compound | | DSS | DSR | DRS | DRR | SR* | RS* |
|---|---|---|---|---|---|---|---|---|
| human | d-rac-pio | k (h⁻¹) | 0.209 | 0.162 | 0.166 | 0.0273 | 0.433 | 0.440 |
| | | $t_{1/2}$ (h) | 1.9 | | 3.6 | | 1.6 | 1.6 |
| | h-S-pio | k (h⁻¹) | — | — | — | — | 0.427 | 0.434 |
| | | $t_{1/2}$ (h) | | — | | — | 1.6 | 1.6 |
| | h-R-pio | k (h⁻¹) | — | — | — | — | 0.439 | 0.447 |
| | | $t_{1/2}$ (h) | | — | | — | 1.6 | 1.6 |
| mouse | d-rac-pio | k (h⁻¹) | 1.038 | 0.118 | 0.141 | 0.218 | 0.924 | 0.743 |
| | | $t_{1/2}$ (h) | 0.60 | | 1.93 | | 0.75 | 0.9 |
| | h-S-pio | k (h⁻¹) | — | — | — | — | 0.979 | 0.792 |
| | | $t_{1/2}$ (h) | | — | | — | 0.7 | 0.9 |
| | h-R-pio | k (h⁻¹) | — | — | — | — | 0.867 | 0.694 |
| | | $t_{1/2}$ (h) | | — | | — | 0.8 | 1.0 |

*enantiomerization rate constant used in analysis of stability of d-rac = average of enantiomerization rate constants obtained by fitting data for stability of h-S and h-R

Example 5

Monoamine Oxidase B (MAO-B) Inhibition Study of (S)-5-({p-[2-(5-ethyl-2-pyridyl)ethoxy]phenyl}methyl)-(5-$^2$H)-1,3-thiazolidine-2,4-dione (d-S-pio) and (R)-5-({p-[2-(5-ethyl-2-pyridyl)ethoxy]phenyl}methyl)-(5-$^2$H)-1,3-thiazolidine-2,4-dione (d-R-pio)

Separate dimethylsulfoxide (DMSO) stock solutions of d-S-pio and d-R-pio were serially diluted in DMSO then mixed with a solution containing 2.5 mU of human recombinant monoamine oxidase B in 90 mM 4-(2-hydroxyethyl)-1-piperazineethanesulfonic acid (HEPES) buffer containing 4.5% glycerol and 9% DMSO. The mixtures were incubated at 22° C. for 5 min. Substrate (D-luciferin derivative) was added, and then the mixture was incubated at 37° C. for 60 min. The reaction was stopped by addition of the detection reagent containing luciferase. Luminescence was read after standing for 60 min at room temperature.

Experiments were performed in duplicate and a positive control (deprenyl) was used to confirm the validity of the assay. Results were expressed as a percentage of the luminescence of the control (enzyme+substrate). IC$_{50}$ values were obtained by fitting experimental data (mean % luminescence as function of concentration) to the Hill equation with variable slope using non-linear regression analysis.

A greater than 5-fold difference in inhibition efficacy was observed between d-R-pio and d-S-pio. The results showed d-S-pio to have an IC$_{50}$=7.6 µM. The results showed d-R-pio to have an IC$_{50}$=1.4 µM.

Example 6

Effect of rac-5-({p-[2-(5-ethyl-2-pyridyl)ethoxy]phenyl}methyl)-1,3-thiazolidine-2,4-dione (h-rac-pio); (S)-5-({p-[2-(5-ethyl-2-pyridyl)ethoxy]phenyl}methyl)-(5-$^2$H)-1,3-thiazolidine-2,4-dione (d-S-pio); and (R)-5-({p-[2-(5-ethyl-2-pyridyl)ethoxy]phenyl}methyl)-(5-$^2$H)-1,3-thiazolidine-2,4-dione (d-R-pio) on mitochondrial respiration in C2C12 cells The effect of treatment of intact C2C12 cells with h-rac-pio, d-S-pio, and d-R-pio on respiration was evaluated under mitochondrial stress conditions in the presence of sodium pyruvate, in an experimental setup similar to that reported by Divakurani et al. in *Proc. Natl. Acad. Sci.* 110 (2013), 5422-5427. Rosiglitazone (10 and 30 µM) and the mitochondrial pyruvate carrier inhibitor UK-5099 (300 nM) were used as positive controls.

On the day before the assay, C2C12 cells were subcultured in XF96 microplates at a density of 20,000 cells per well. After overnight incubation (37° C., 5% CO$_2$), the cells were washed 3 times with assay medium (Seahorse medium (Seahorse Bioscience, North Billerica, Mass.) containing 10 mM sodium pyruvate, pH 7.4). Compounds, d-S-pio, d-R-pio, or h-rac-pio (3, 10, or 30 µM final concentration), were added to the wells and the plates were incubated at 37° C. (without CO$_2$). A full mitochondrial stress test was performed on the XF96 Extracellular Flux Analyzer (Seahorse Biosciences), including injection of the ATP synthase inhibitor oligomycin (3.5 µM final), the oxidative phosphorylation uncoupling agent FCCP (carbonyl cyanide 4-(trifluoromethoxy)phenylhydrazone, 1 µM final concentration), and the complex III inhibitor antimycin A (2.5 µM final). Incubation times of 15, 30, or 90 min were used prior to measurement of maximal respiration, i.e., until addition of FCCP. Injection of FCCP always occurred 15 min after the start of the respirometry assay. Maximal respiration as oxygen consumption rates (pmoles O$_2$/min) was measured for each compound, at each concentration, and each time point in three separate experiments.

Figure 4:
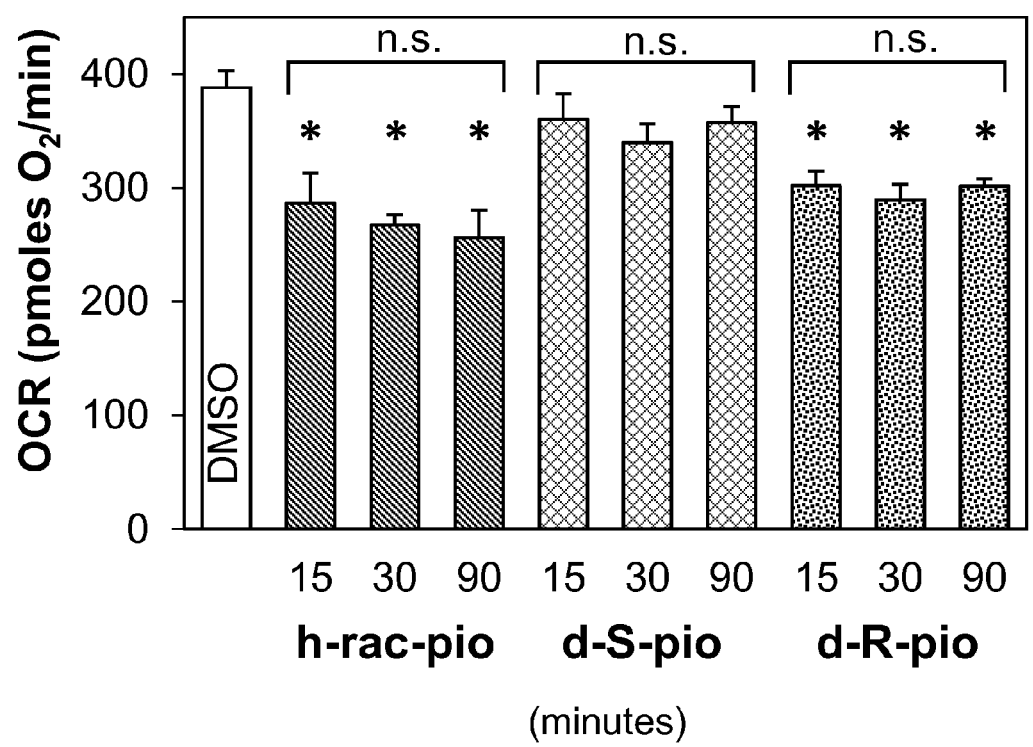
FIG. 4 is a bar graph depicting maximal respiration as oxygen consumption rate (OCR in pmoles $O_2$/min) of C2C12 cells treated with h-rac-pio, d-S-pio, or d-R-pio at 30 µM for 15, 30, or 90 min compared to the OCR in vehicle-treated cells, as further described in Example 6.

Results for the incubation with compounds at 30 µM concentration are presented in FIG. 4, which shows maximal respiration as oxygen consumption rate (OCR in pmoles O$_2$/min) of C2C12 cells treated with h-rac-pio, d-S-pio, or d-R-pio at 30 µM for 15, 30, or 90 minutes compared to the OCR in vehicle-treated cells (average of all repeats and time points); statistical analysis: one-way ANOVA with Newman-Keuls post-test; * $P<0.05$; n.s. means not statistically significant. Both h-rac-pio and d-R-pio inhibited maximal respiration while no significant measurable effect was observed for d-S-pio.

Example 7

Pharmacokinetics (PK) of rac-5-({p-[2-(5-ethyl-2-pyridyl)ethoxy]phenyl}methyl)-1,3-thiazolidine-2,4-dione (h-rac-pio); (R)-5-({p-[2-(5-ethyl-2-pyridyl)ethoxy]phenyl}methyl)-(5-$^2$H)-1,3-thiazolidine-2,4-dione (d-R-pio); and (S)-5-({p-[2-(5-ethyl-2-pyridyl)ethoxy]phenyl}methyl)-(5-$^2$H)-1,3-thiazolidine-2,4-dione (d-S-pio)

Part I—Experimental Procedure

Male C57BL/6 mice (8-10 weeks of age) were randomly divided into 3 groups of n=24 animals and administered 30 mg/kg h-rac-pio, 15 mg/kg d-S-pio, or 15 mg/kg d-R-pio (in a 0.25% carboxymethylcellulose solution prepared daily and used within 1 h of preparation) by oral gavage once a day for 5 days. Blood samples 0.5 mL) were collected in K2EDTA tubes on day 5 from n=3 animals per group per time point: pre-dose or 0.25, 0.5, 1, 2, 4, 8, or 24 h post-dose by retrobulbar bleeding under light anesthesia (isoflurane). Animals were then euthanized. Plasma was separated by centrifugation and stored at −80° C. until analyzed.

Samples were processed and analyzed by chiral HPLC/MS-MS (ISTD: d$_4$-pioglitazone) as described in Example 4. Peak areas were normalized to the peak area of the ISTD and normalized peak areas for deuterated enantiomers d-S-pio and d-R-pio were corrected for interference from the isotopic peak of the corresponding protonated enantiomer. Concentrations were calculated by interpolation on standard curves generated from mouse plasma samples spiked with known concentrations of the pure analytes. Data was plotted in Excel 2013 (Microsoft Corp, Redmond, Wash.) and analyzed within Excel using the PKSolver add-in (version 2.0, as described in Zhang Y. et al. in *Comput. Methods Programs Biomed.* 99 (2010), 306-314) to determine PK parameters including exposure (as area under the curve, AUC) and elimination half-life ($t_{1/2}$).

Part II—Results

Figure 5A:
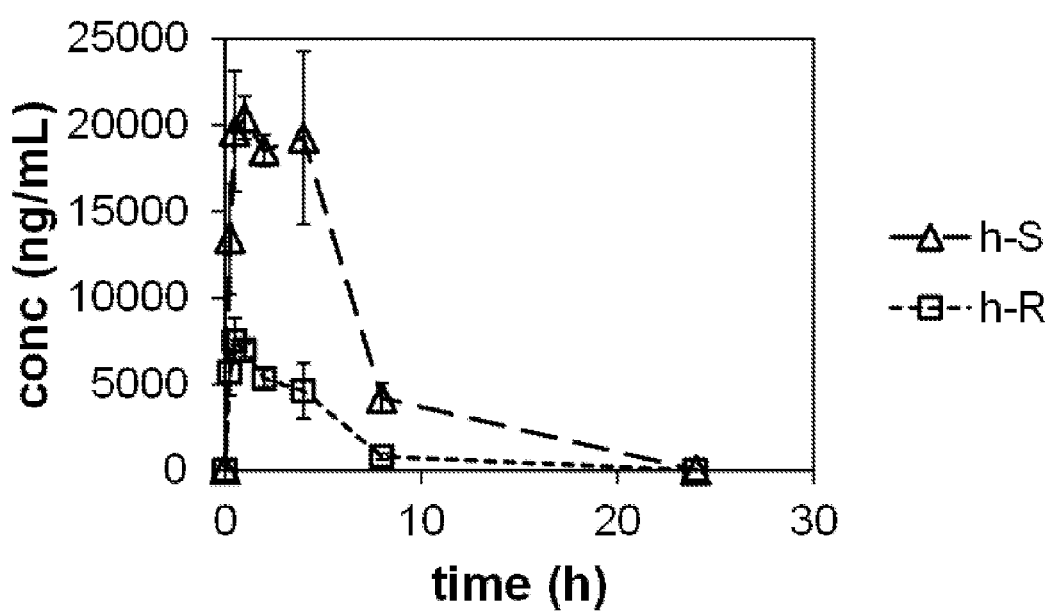
FIG. 5A is a line graph depicting PK profiles for the enantiomers of pioglitazone in mice administered h-rac-pio (30 mg/kg) by oral gavage daily for 5 days; (S)-enantiomer—hollow triangles, dashed line; (R)-enantiomer—hollow squares, dotted line; as further described in Example 7.
Figure 5B:
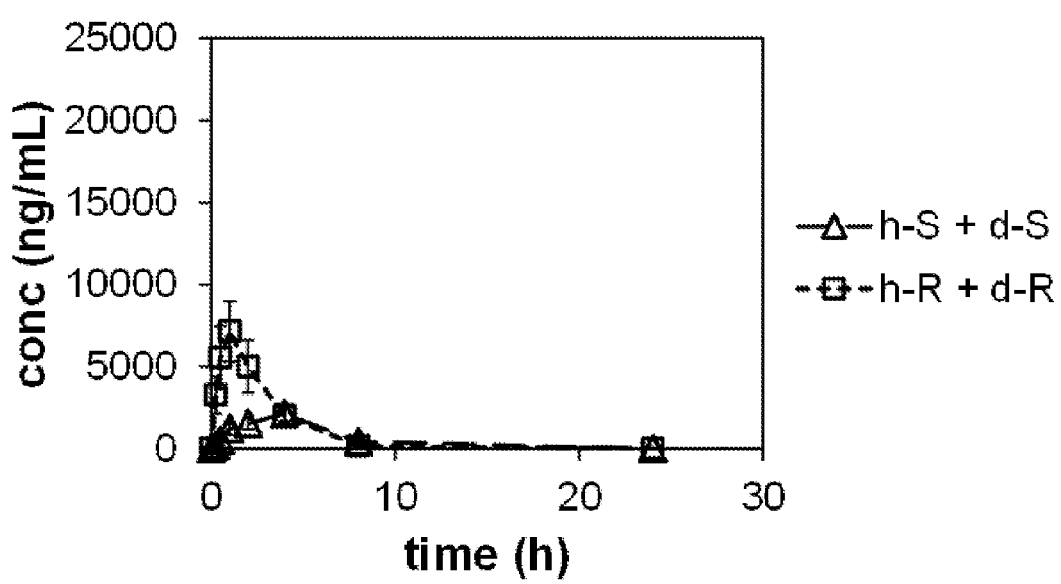
FIG. 5B is a line graph depicting PK profiles for the enantiomers of pioglitazone in mice administered d-R-pio (15 mg/kg) by oral gavage daily for 5 days; (S)-enantiomer—hollow triangles, dashed line; (R)-enantiomer—hollow squares, dotted line; each curve represents the sum of corresponding isotopomers ((S)-enantiomer: h-S-pio+d-S-pio, and (R)-enantiomer: h-R-pio+d-R-pio), as further described in Example 7.
Figure 5C:
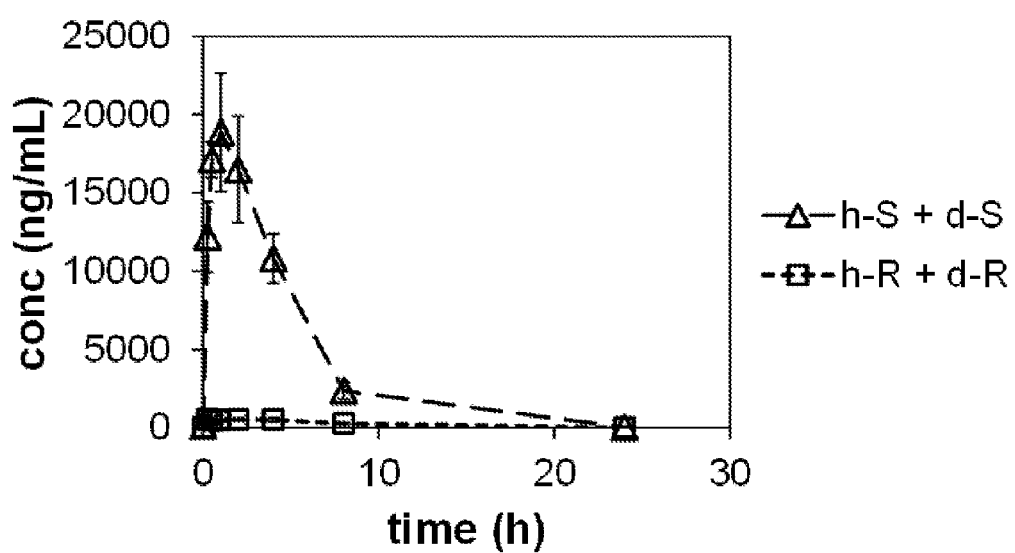
FIG. 5C is a line graph depicting PK profiles for the enantiomers of pioglitazone in mice administered d-S-pio (15 mg/kg) by oral gavage daily for 5 days; (S)-enantiomer—hollow triangles, dashed line; (R)-enantiomer—hollow squares, dotted line; each curve represents the sum of corresponding isotopomers ((S)-enantiomer: h-S-pio+d-S-pio, and (R)-enantiomer: h-R-pio+d-R-pio), as further described in Example 7.

PK profiles determined using the above procedure are shown in FIGS. 5A-C. Selected PK parameters ($C_{max}$, $t_{max}$, AUC$_{0-inf}$, and $t_{1/2}$) for the enantiomers of protonated and deuterated pioglitazone in mice after oral gavage of h-rac-pio, d-S-pio, or d-R-pio are presented in Table 7.

Exposure (as area under the curve, AUC) to the enantiomers of h-rac-pio was stereoselective in animals dosed with h-rac-pio (1:1 mixture of h-S-pio and h-R-pio) resulting in a 4:1 ratio of h-S-pio to h-R-pio. Dosing d-R-pio resulted in a 10-fold decrease in exposure to the (S)-enantiomer, while exposure to the (R)-enantiomer decreased by only 1.7-fold.

Dosing d-R-pio resulted in a reversal of the relative exposure (S:R=3:5) compared to what was observed in mice dosed with h-rac-pio. Similarly, dosing d-S-pio resulted in a 7-fold decrease in exposure to the (R)-enantiomer (vs. dosing h-rac-pio) while exposure to the (S)-enantiomer decreased by 1.5-fold.

TABLE 7

| Compound | $C_{max}$ (ng/mL) | | | | $t_{max}$ (h) | | | |
| --- | --- | --- | --- | --- | --- | --- | --- | --- |
| | h-S | h-R | d-S | d-R | h-S | h-R | d-S | d-R |
| h-rac-pio | 20433 | 7510 | — | — | 1 | 0.5 | — | — |
| d-S-pio | 2183 | 574 | 17133 | — | 4 | 0.25 | 1 | — |
| d-R-pio | 2127 | 805 | 147 | 6360 | 4 | 1 | 1 | 1 |

| Compound | $AUC_{0-inf}$ (ng · h/mL) | | | | $t_{1/2}$ (h) | | | |
| --- | --- | --- | --- | --- | --- | --- | --- | --- |
| | h-S | h-R | d-S | d-R | h-S | h-R | d-S | d-R |
| h-rac-pio | 154240 | 39702 | — | — | 2.3 | 2.5 | — | — |
| d-S-pio | 22344 | 5865 | 82708 | — | 3.1 | 3.2 | 2.3 | — |
| d-R-pio | 14036 | 4850 | 375 | 18892 | 2.5 | 2.5 | 0.8 | 1.8 |

Example 8

Effect of rac-5-({p-[2-(5-ethyl-2-pyridyl)ethoxy]phenyl}methyl)-1,3-thiazolidine-2,4-dione (h-rac-pio); (R)-5-({p-[2-(5-ethyl-2-pyridyl)ethoxy]phenyl}methyl)-(5-$^2$H)-1,3-thiazolidine-2,4-dione (d-R-pio); (s)-5-({p-[2-(5-ethyl-2-pyridyl)ethoxy]phenyl}methyl)-(5-$^2$H)-1,3-thiazolidine-2,4-dione (d-S-pio) on diabetes and inflammation in the db/db mouse model of type II diabetes Part I—Experimental Procedure Transgenic db/db mice (Jackson Laboratory, Bar Harbor, Me.; n=8 per dose group, 8 weeks of age at study start) were dosed daily by oral gavage for 10 days with vehicle (0.25% carboxymethylcellulose in water), h-rac-pio (30 mg/kg), d-S-pio (20 mg/kg), or d-R-pio (20 mg/kg). Dosing solutions were prepared daily and used within 1 h of preparation. Body weights were measured throughout the study. Non-fasting blood glucose (10 μL by tail snip) was measured 4 hours prior to first dose, and animals were sorted and assigned to groups based on this measure. Mice were also bled throughout the study through tail snip for blood glucose determination at 1 h post-first dose, 1 h post-fifth dose, 1 h post-eighth dose, and 1 h post-last dose. Animals were euthanized 1 h post-last dose on day 10. A terminal blood sample was collected for determination of serum levels of cholesterol, triglycerides, free fatty acids, adiponectin, serum amyloid A, and cytokines IL-1β, IL-6, TNF-α, and MCP-1, using standard analytical methods. Quantitative results were analyzed by statistical methods using, as appropriate, one- or two-way ANOVA or Kruskal-Wallis tests for differences followed by Sidak's, Dunnett's, or Dunn's post-test to determine differences vs. vehicle-treated control animals. All graphs were generated with GraphPad Prism version 6.0.2 (GraphPad Software, Inc., La Jolla, Calif.).

Part II—Results

No significant differences in body weight were observed between dose groups. No overt signs of toxicity were seen in any animal of any dose group.

Figure 6:
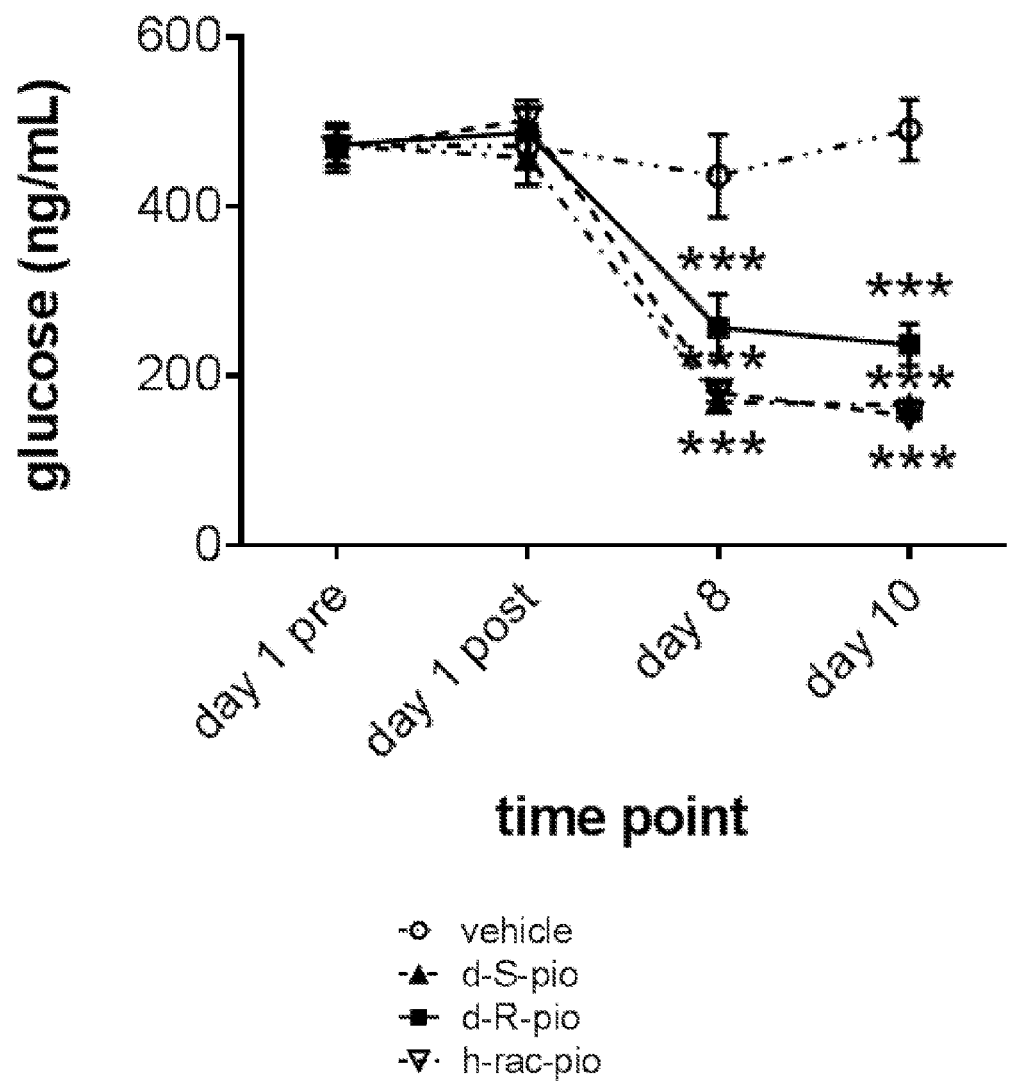
FIG. 6 is a line graph depicting the amount of non-fasted blood glucose (ng/mL) in db/db mice dosed daily by oral gavage with vehicle (hollow circles), 20 mg/kg d-S-pio (filled triangles), 20 mg/kg d-R-pio (filled squares), or 30 mg/kg h-rac-pio (hollow triangles) measured on day one at 4 hours pre-first dose, and on days one, eight, and ten, 1 hour post-dose (2-way repeated measures ANOVA with Sidak post-test, *** $P<0.001$), where the abbreviation "day 1 pre" refers to results from measurements taken on day one at 4 hours pre-first dose, and the abbreviation "day 1 post" refers to results from measurements taken on day one at 1 hour post-dose; as further described in Example 8.

Blood glucose data are presented in FIG. 6, which shows the amount of non-fasted blood glucose (ng/mL) in db/db mice dosed daily by oral gavage with vehicle (hollow circles), 20 mg/kg d-S-pio (filled triangles), 20 mg/kg d-R-pio (filled squares), or 30 mg/kg h-rac-pio (hollow triangles) measured on day one at 4 hours pre-first dose, and on days one, eight, and ten, 1 hour post-dose (2-way repeated measures ANOVA with Sidak post-test, *** P<0.001).

Figure 7A:
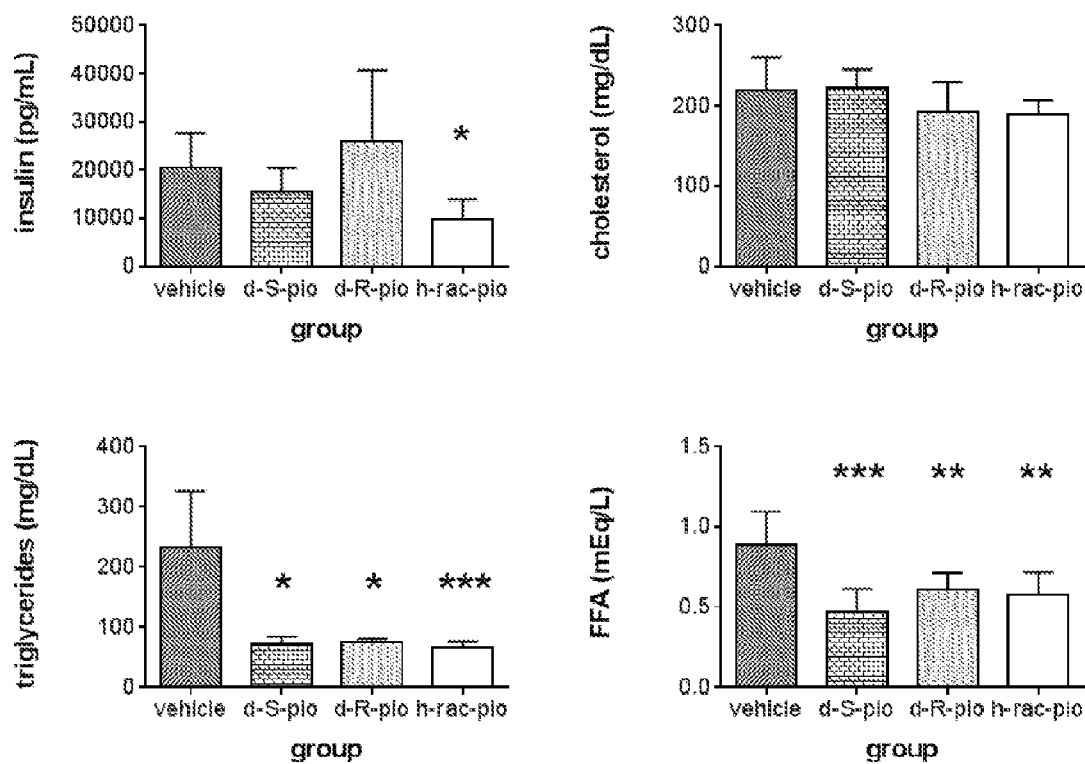
FIGS. 7A-C are line graphs depicting the effect of 10-day, daily oral administration of vehicle, d-S-pio (20 mg/kg), d-R-pio (20 mg/kg), or h-rac-pio (30 mg/kg) to db/db mice on certain metabolic disease biomarkers (i.e., insulin, cholesterol, triglycerides, non-essential fatty acids, adiponectin, and inflammatory biomarkers (i.e., IL-1β, IL-6, TNF-α, MCP-1, and serum amyloid A) (Kruskal-Wallis test with Dunn's post-test against vehicle, * $P<0.05$,  $P<0.01$, * $P<0.001$, and **** $P<0.0001$, for insulin, cholesterol, triglycerides, non-essential fatty acids, adiponectin, MCP-1; one-tailed unpaired t-test against vehicle, * $P<0.05$, for IL-1β, IL-6, TNF-α, and serum amyloid A), as further described in Example 8.
Figure 7B:
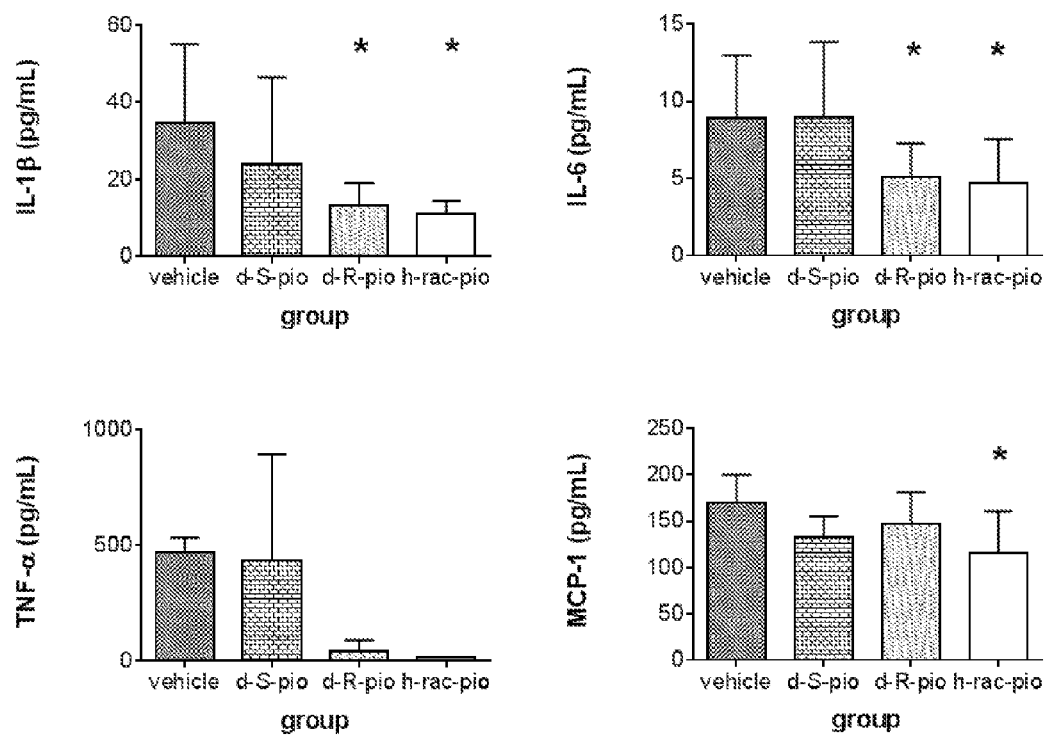
Figure 7C:
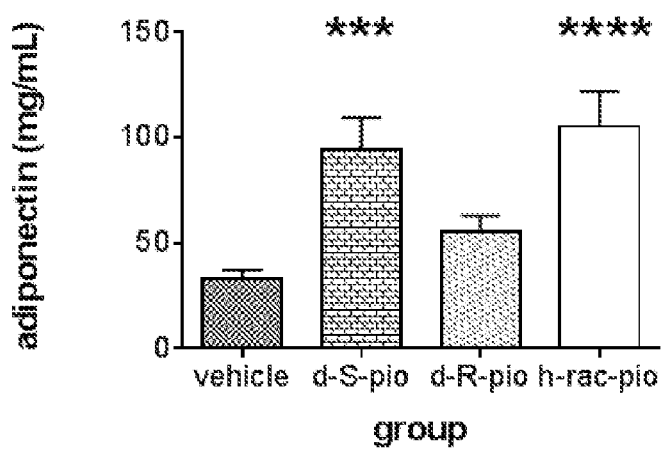
Figure 7C:
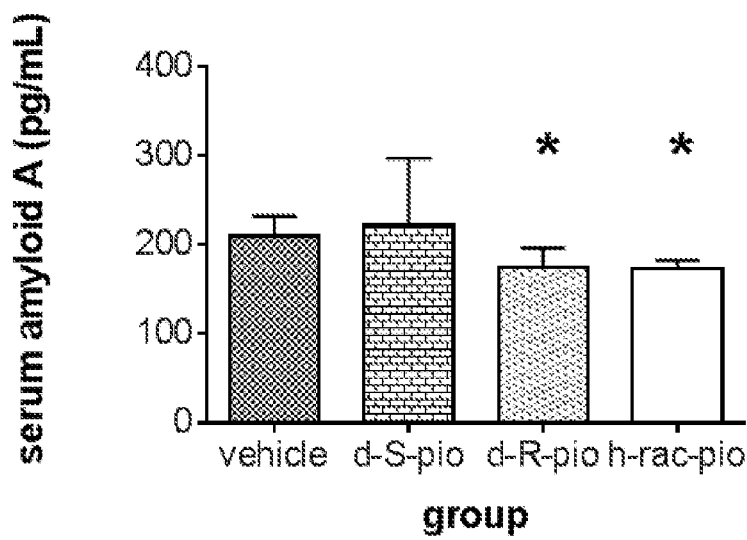

Effects of h-rac-pio, d-S-pio, and d-R-pio on metabolic disease biomarkers, adiponectin, and inflammatory biomarkers are summarized in FIGS. 7A-C, which illustrate the effect of 10-day, daily oral administration of vehicle, d-S-pio (20 mg/kg), d-R-pio (20 mg/kg), or h-rac-pio (30 mg/kg) to db/db mice on certain metabolic disease biomarkers (i.e., insulin, cholesterol, triglycerides, non-essential fatty acids), adiponectin, and inflammatory biomarkers (i.e., IL-1β, IL-6, TNF-α, MCP-1, and serum amyloid A) (Kruskal-Wallis test with Dunn's post-test against vehicle, * P<0.05,  P<0.01, * P<0.001, and **** P<0.0001, for insulin, cholesterol, triglycerides, non-essential fatty acids, adiponectin, MCP-1; one-tailed unpaired t-test against vehicle, * P<0.05, for IL-1β, IL-6, TNF-α, and serum amyloid A).

The results show that both d-S-pio and d-R-pio decreased non-fasted blood glucose to approximately the same extent as h-rac-pio. The same was observed for serum triglycerides, while a similar trend was observed for non-essential fatty acids.

Only d-S-pio and h-rac-pio significantly increased adiponectin. Only h-rac-pio significantly decreased insulin. Inflammatory biomarkers were similarly decreased by d-R-pio and h-rac-pio: trending for cytokines IL-1β, IL-6, and TNF-α, and statistically significant for serum amyloid A.

Example 9

Figure 8:
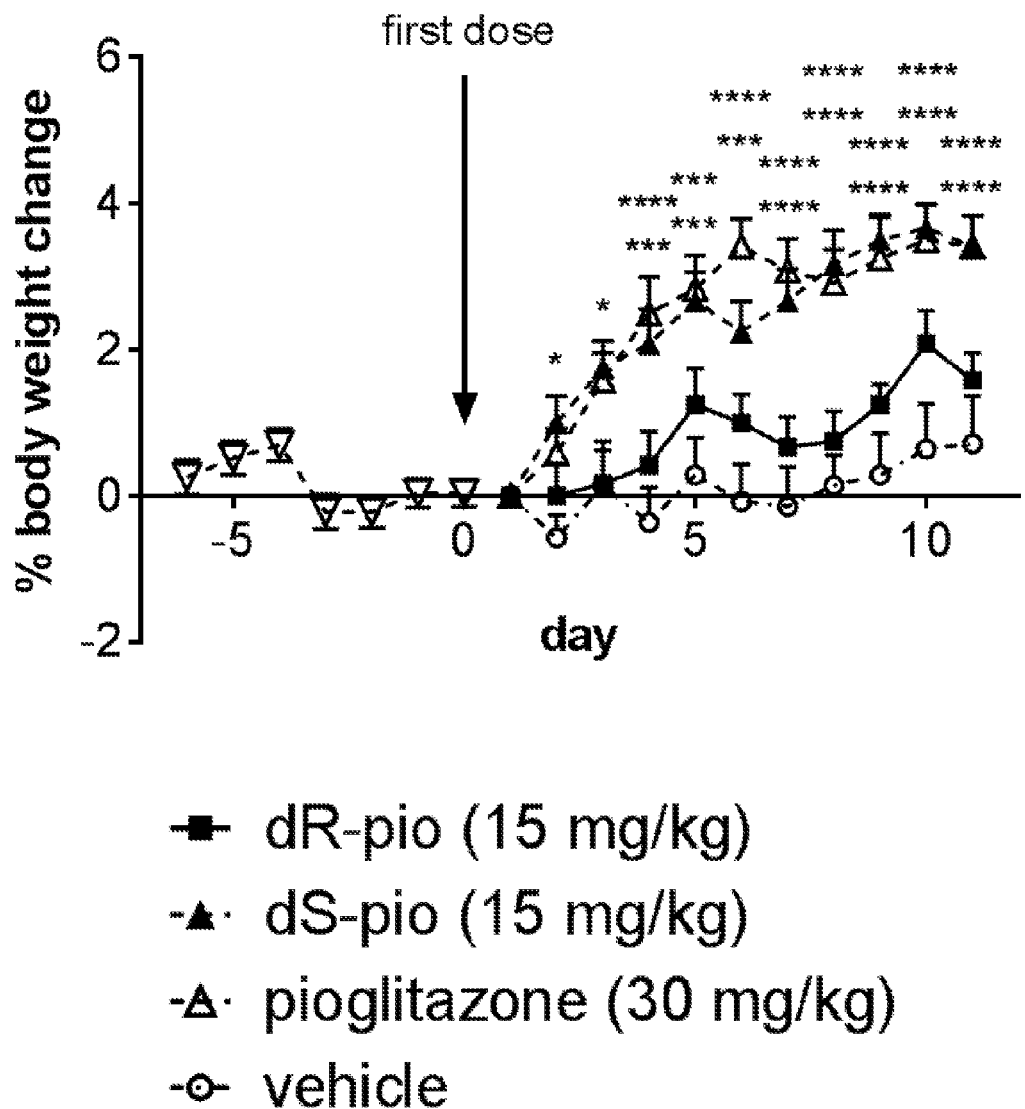
FIG. 8 is a line graph depicting the effect of twice daily dosing with vehicle (hollow circles), h-rac-pio (30 mg/kg overall daily dose, hollow triangles), d-S-pio (15 mg/kg overall daily dose, filled triangles), and d-R-pio (15 mg/kg overall daily dose, filled squares) on body weight, expressed as percent body weight difference versus day 1 body weight (mean±SEM) in male C57BL/6J mice (n=14 mice in vehicle group, n=12 each in h-rac-pio, d-S-pio, and d-R-pio groups; ANOVA statistical analysis with multiple comparison Dunnett's post-test, * $P<0.05$,  $P<0.01$, * $P<0.001$), as further described in Example 9.

Effect of rac-5-({p-[2-(5-ethyl-2-pyridyl)ethoxy]phenyl}methyl)-1,3-thiazolidine-2,4-dione (h-rac-pio); (R)-5-({p-[2-(5-ethyl-2-pyridyl)ethoxy]phenyl}methyl)-(5-$^2$H)-1,3-thiazolidine-2,4-dione (d-R-pio); and (S)-5-({p-[2-(5-ethyl-2-pyridyl)ethoxy]phenyl}methyl)-(5-$^2$H)-1,3-thiazolidine-2,4-dione (d-S-pio) on body weight gain in male C57BL/6J mice on a standard diet Part I—Experimental Procedure Male C57BL/6J mice (about 28 g body weight) were acclimated singly-housed for one week to a reverse light/dark cycle with free access to water and standard maintenance diet. Animals were then handled daily for one week followed by another 7 days of twice daily dosing with vehicle (0.5% methylcellulose in water) by oral gavage. After the habituation period the mice were allocated to 1 of 4 dosing groups (n=12 to 14 animals per group; 14 for vehicle control) on the basis of body weight, and food and water intake. Animals were then dosed twice daily by oral gavage with vehicle, h-rac-pio (30 mg/kg overall daily dose, i.e., two doses of 15 mg/kg daily), d-S-pio (15 mg/kg overall daily dose, i.e., two doses of 7.5 mg/kg daily), or d-R-pio (15 mg/kg overall daily dose, i.e., two doses of 7.5 mg/kg daily) for 11 days at the beginning and end of the dark phase. Dosing solutions (0.5% methylcellulose in water adjusted to pH~7 for d-S-pio and d-R-pio) were prepared twice daily and used within 1 h of preparation. Body weights were measured twice daily, prior to each dosing, to adjust individual dosing volumes to actual body weights. The morning body weights were recorded and are presented in FIG. 8 as percent body weight difference versus day 1.

Part II—Results

Dosing with h-rac-pio and d-S-pio resulted in a statistically significant increase in percent body weight difference compared to dosing with vehicle. Oral gavage with d-R-pio did not increase percent body weight difference over vehicle. Results are depicted graphically in FIG. 8, which shows the effect of twice daily dosing with vehicle (hollow circles), h-rac-pio (30 mg/kg overall daily dose, hollow triangles), d-S-pio (15 mg/kg overall daily dose, filled triangles), and d-R-pio (15 mg/kg overall daily dose, filled squares) on body weight, expressed as percent body weight difference versus day 1 body weight (mean±SEM) in male C57BL/6J mice (n=14 mice in vehicle group, n=12 each in h-rac-pio, d-S-pio, and d-R-pio groups; ANOVA statistical analysis with multiple comparison Dunnett's post-test, * P<0.05,  P<0.01, * P<0.001).

INCORPORATION BY REFERENCE

All references listed herein are individually incorporated in their entirety by reference.

EQUIVALENTS

Numerous modifications and variations of the invention are possible in light of the above teachings. It is therefore to be understood that within the scope of the appended claims, the invention may be practiced otherwise that as specifically described herein.

What is claimed is:

1. A method of treating a neurological disorder selected from the group consisting of Parkinson's disease, amyotrophic lateral sclerosis, Friedreich's ataxia, autism spectrum disorder, depression, mild cognitive impairment, Down syndrome, neurodegeneration, adrenoleukodystrophy, Huntington's disease, substance abuse, neuronal injury, and major depression or bipolar disorder cormorbid with metabolic syndrome, comprising administering to a patient in need thereof a therapeutically effective amount of a deuterium-enriched compound of Formula I having an optical purity of at least 75% enantiomeric excess to treat the neurological disorder, wherein Formula I is represented by:

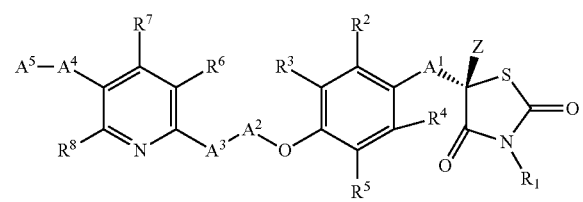

(I)

or a pharmaceutically acceptable salt thereof, wherein:
$A^1$, $A^2$, $A^3$, and $A^4$ are independently —C($R^9$)($R^{10}$)—;
$A^5$ is —C($R^{11}$)($R^{12}$)($R^{13}$);
$R^1$, $R^2$, $R^3$, $R^4$, $R^5$, $R^6$, $R^7$, and $R^8$ are independently H or D;
$R^9$, $R^{10}$, $R^{11}$, $R^{12}$, and $R^{13}$ each represent independently for each occurrence H or D; and
Z is H or D, provided that the abundance of deuterium in Z is at least 30.

2. The method of claim 1, wherein the disorder is adrenoleukodystrophy.

3. The method of claim 2, wherein the compound is a compound of Formula I-A having an optical purity of at least 75% enantiomeric excess, wherein Formula I-A is represented by:

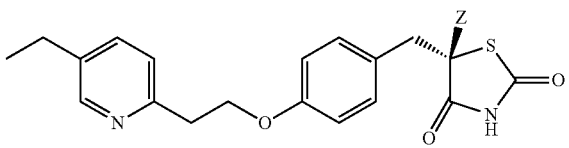

(I-A)

or a pharmaceutically acceptable salt thereof, wherein Z is H or D, provided that the abundance of deuterium in Z is at least 30%.

4. A method of treating a neurological disorder selected from the group consisting of Parkinson's disease, amyotrophic lateral sclerosis, Friedreich's ataxia, autism spectrum disorder, depression, mild cognitive impairment, Down syndrome, neurodegeneration, adrenoleukodystrophy, Huntington's disease, substance abuse, neuronal injury, and major depression or bipolar disorder comorbid with metabolic syndrome, comprising administering to a patient in need thereof a therapeutically effective amount of a deuterium-enriched compound of Formula II having an optical purity of at least 75% enantiomeric excess to treat the neurological disorder, wherein Formula II is represented by:

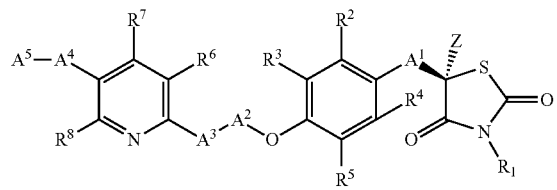

(II)

or a pharmaceutically acceptable salt thereof, wherein:
$A^1$, $A^2$, $A^3$, and $A^4$ are independently —C($R^9$)($R^{10}$)—;
$A^5$ is —C($R^{11}$)($R^{12}$)($R^{13}$);
$R^1$, $R^2$, $R^3$, $R^4$, $R^5$, $R^6$, $R^7$, and $R^8$ are independently H or D;
$R^9$, $R^{10}$, $R^{11}$, $R^{12}$, and $R^{13}$ each represent independently for each occurrence H or D; and
Z is H or D, provided that the abundance of deuterium in Z is at least 30%.

5. The method of claim 4, wherein the disorder is adrenoleukodystrophy.

6. The method of claim 5, wherein the deuterium-enriched compound is administered orally.

7. The method of claim 5, wherein the compound is a compound of Formula II-A having an optical purity of at least 75% enantiomeric excess, wherein Formula II-A is represented by:

(II-A)

*[chemical structure]* or a pharmaceutically acceptable salt thereof, wherein Z is H or D, provided that the abundance of deuterium in Z is at least 30%.

8. The method of claim 7, wherein the deuterium-enriched compound is in the form of a pharmaceutically acceptable salt.

9. The method of claim 8, wherein the pharmaceutically acceptable salt is a hydrochloride salt.

10. The method of claim 7, wherein the abundance of deuterium in Z is at least 75%.

11. The method of claim 7, wherein the abundance of deuterium in Z is at least 90%.

12. The method of claim 11, wherein the compound has an enantiomeric excess of at least 85%.

13. The method of claim 5, wherein the compound is:

*[chemical structure]* or pharmaceutically acceptable salt thereof, each having an optical purity of at least 90% enantiomeric excess.

14. The method of claim 5, wherein the compound is:

*[chemical structure]* having an optical purity of at least 90% enantiomeric excess.

15. The method of claim 5, wherein the compound is:

*[chemical structure]* hydrochloride having an optical purity of at least 90% enantiomeric excess.

16. The method of claim 5, wherein the compound is:

*[chemical structure]* or pharmaceutically acceptable salt thereof, each having an optical purity of at least 95% enantiomeric excess.

17. The method of claim 5, wherein the compound is:

*[chemical structure]* having an optical purity of at least 95% enantiomeric excess.

18. The method of claim 5, wherein the compound is:

*[chemical structure]* hydrochloride having an optical purity of at least 95% enantiomeric excess.

19. The method of claim 12, wherein the deuterium-enriched compound is administered orally.

20. The method of claim 16, wherein the deuterium-enriched compound is administered orally.

* * * * *